(12) United States Patent
Zhong et al.

(10) Patent No.: US 10,653,794 B2
(45) Date of Patent: May 19, 2020

(54) CAPPED AND UNCAPPED ANTIBODY CYSTEINES, AND THEIR USE IN ANTIBODY-DRUG CONJUGATION

(71) Applicant: PFIZER INC., New York, NY (US)

(72) Inventors: Xiaotian Zhong, Wayland, MA (US); Amarnauth Shastrie Prashad, New City, NY (US); Ronald William Kriz, Northborough, MA (US); Tao He, Acton, MA (US); Will Somers, Lexington, MA (US); Wenge Wang, Andover, MA (US); Leo Joseph Letendre, Oakdale, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/748,268

(22) PCT Filed: Aug. 9, 2016

(86) PCT No.: PCT/IB2016/054789
§ 371 (c)(1),
(2) Date: Jan. 29, 2018

(87) PCT Pub. No.: WO2017/025897
PCT Pub. Date: Feb. 16, 2017

(65) Prior Publication Data
US 2019/0030183 A1    Jan. 31, 2019

Related U.S. Application Data

(60) Provisional application No. 62/204,005, filed on Aug. 12, 2015.

(51) Int. Cl.
*A61K 47/68* (2017.01)
*C07K 16/00* (2006.01)
*C07K 16/30* (2006.01)
*A61K 38/05* (2006.01)

(52) U.S. Cl.
CPC .......... *A61K 47/6889* (2017.08); *A61K 38/05* (2013.01); *A61K 47/68* (2017.08); *A61K 47/6817* (2017.08); *A61K 47/6851* (2017.08); *A61K 47/6855* (2017.08); *C07K 16/00* (2013.01); *C07K 16/30* (2013.01); *C07K 2317/14* (2013.01); *C07K 2317/40* (2013.01); *C07K 2317/526* (2013.01); *C07K 2317/55* (2013.01); *C07K 2317/94* (2013.01)

(58) Field of Classification Search
CPC ............ A61K 47/6889; A61K 47/6855; A61K 47/68; A61K 38/05; A61K 47/6817; A61K 47/6851; C07K 16/30; C07K 16/00; C07K 2317/94; C07K 2317/55; C07K 2317/526; C07K 2317/40; C07K 2317/14
See application file for complete search history.

(56) References Cited

U.S. PATENT DOCUMENTS

| 7,018,809 | B1 * | 3/2006 | Carter | C07K 16/00 435/488 |
|---|---|---|---|---|
| 2005/0123532 | A1 * | 6/2005 | Kouno | C12N 1/00 424/130.1 |
| 2009/0053786 | A1 * | 2/2009 | Kao | A61K 39/39591 435/184 |
| 2011/0033378 | A1 * | 2/2011 | Dimasi | A61K 51/1027 424/1.49 |
| 2011/0124054 | A1 * | 5/2011 | Olejnik | C12Q 1/6825 435/91.5 |
| 2011/0301334 | A1 | 12/2011 | Bhakta et al. | |
| 2012/0264916 | A1 * | 10/2012 | Evans | C07K 16/00 530/387.1 |
| 2013/0017200 | A1 * | 1/2013 | Scheer | C07K 16/283 424/136.1 |
| 2015/0125472 | A1 * | 5/2015 | Damelin | A61K 31/704 424/178.1 |

FOREIGN PATENT DOCUMENTS

| EP | 2527429 A1 | 11/2012 | |
| EP | 2818480 A1 | 12/2014 | |
| WO | 0042175 | 7/2000 | |
| WO | WO-0042175 A1 * | 7/2000 | ........... C07K 14/505 |
| WO | 2009092011 A1 | 7/2009 | |

(Continued)

OTHER PUBLICATIONS

Brenan et al., Science 229: 81-83, 1985 (Year: 1985).*
Doromina et al., Bioconjugate Chem 17: 114-124 (Year: 2006).*
Tris(3-sulfophenyl)phosphinet triisodium salt, www.chemspider.com/Chemical-structure.3552062.html (Year: 2019).*
American Type Culture Collection, "Formulation for Dulbecco's Modified Eagle's Medium (DMEM) ATCC(R) 30-2002", p. 1, 2002.
Banhegyi, et al., "Preferential Transport of Glutathione versus Glutathione Disulfide in Rat Liver Microsomal Vesicles*", Journal of Biological Chemistry, 1999, 12213-12216, 274(18).
Banks, et al., "Removal of Cysteinylation from an Unpaired Sulthydryl in the Variable Region of a Recombinant Monoclonal IgG1 Antibody Improves Homogeneity, Stability, and Biological Activity", 2008, 764-779, 97(2).
Barford, et al., "The role of cysteine residues as redox-sensitive regulatory switches", Current Opinion in Structural Biology, 2004, 679-686, 14.

(Continued)

*Primary Examiner* — Phuong Huynh
(74) *Attorney, Agent, or Firm* — David Rubin

(57) ABSTRACT

An antibody production process in mammalian cells in which engineered unpaired cysteine residues are post-translationally modified and capped with particular chemical entities, which capped antibodies are well suited to further site-specific conjugation steps to form antibody-drug conjugates (ADCs) or protein drug conjugates; ADCs produced using these capped antibodies including in particular ADCs formed by the selective reduction of the capped antibodies' cysteine residues, and ADCs formed using chemical handles such as aldehyde/azide/alkyne biorthogonal groups, which permit additional drug conjugation chemistry; and uncapped antibodies produced by cells in low cysteine, cysteine and glutathione media, and ADCs produced via direct conjugation to these uncapped antibodies.

6 Claims, 18 Drawing Sheets

(56) References Cited

FOREIGN PATENT DOCUMENTS

| WO | 2015085003 A1 | 6/2015 |
|---|---|---|
| WO | 2015110935 A1 | 7/2015 |

OTHER PUBLICATIONS

Bass et al., "A Major Fraction of Endoplasmic Reticulum-located Glutathione Is Present as Mixed Disulfides with Protein*", Journal of Biological Chemistry, 2004, 5257-5262, 279(7).
Buchanan, et al., "Engineering a therapeutic IgC molecule to address cysteinylation, aggregation and enhance thermal stability and expression", mAbs, 2013, 255-262, 5:2.
Chakravarthi, et al., "The role of glutathione in disulphide bond formation and endoplasmic-reticulum-generated oxidative stress", EMBO Reports, 2006, 271-275, 7.
Chen, et al., "Charge-based analysis of antibodies with engineered cysteines", mAbs, 2009, 563-571, 1:6.
Ehrenmann, et al., "IMGT/3Dstructure-DB and IMGT/DomainGapAlign: a database and a tool for immunoglobulins or antibodies, T cell receptors, MHC, IgSF and MhcSF". Nucleic Acids Research, 2010, D301-D307, 38.
Florence, "Degradation of protein disulphide bonds in dilute alkali", Biochem J., 1980, 507-520, 189.
Frand, et al., "The ER01 Gene of Yeast Is Required for Oxidation of Protein Dithiols in the Endoplasmic Reticulum", Molecular Cell, 1998, 161-170, 1.
Frand, et al., "Pathways for protein disulphide bond formation", Cell Biology, 203-210, 10.
Gadgil, et al., "Identification of cysteinylation of a free cysteine in the Fab region of a recombinant monoclonal IgG1 antibody using Lys-C limited proteolysis coupled with LC/MS analysis", Analytical Biochemistry, 2006, 165-174, 355.
Georgiou, et al., "How to Flip the (Redox) Switch", Cell, 2002, 607-610, 111.
Gomez, et al., "Triple Light Chain Antibodies: Factors That Influence Its Formation in Cell Culture", Biotechnology and Bioengineering, 2010, 748-760, 105.
Hwang, et al., "Oxidized Redox State of Glutathione in the Endoplasmic Reticulum", Science, 1992, 1496-1502, 257.
Jessop et al., "Glutathione Directly Reduces an Oxidoreductase in the Endoplasmic Reticulum of Mammalian Cells*", The Journal of Biological Chemistry, 2004, 55341-55347, 279(53).
Johnson et al., "Development of a Humanized Monoclonal Antibody (MEDI-493) with Potent In Vitro and In Vivo Activity against Respiratory Syncytial Virus", The Journal of Infectious Diseases, 1997, 1215-1224, 176.
Jordan et al., "Extracellular Disulfide Exchange and the Regulation of Cellular Function", Antioxidants and Redox Signaling, 2006, 312-324, 8.
Junutula et al., "Engineered Thio-Trastuzumab-DM1 Conjugate with an Improved Therapeutic Index to Target Human Epidermal Growth Factor Receptor 2-Postitive Breast Cancer", Clinical Cancer Research, 2010, 4769-4778, 16 (19).
Junutula et al., "Site-specific conjugation of a cytotoxic drug to an antibody improves the therapeutic index", Nature Biotechnology. 2008, 925-932, 26(8).
Kao et al., "Mechanism of Antibody Reduction in Cell Culture Production Processes", Biotechnology & Bioengineering,2010, 622-632, 107(4).
Kopito et al., "Aggresomes and Russell bodies", EMBO Reports, 2000, 225-231, 1(3).
Kroon, et al., "Identification of Sites of Degradation in a Therapeutic Monoclonal Antibody by Peptide Mapping", Pharmaceutical Research, 1992, 1386-1393, 9(11).
Kung et al., "SGN-CD33A: a novel CD33-targeting antibody-drug conjugate using a pyrrolobenzodiazepine dimer is active in models of drug-resistant AML", Blood, 2013, 1455-1463, 122(8).
Le Gall, et al., "The Endoplasmic Reticulum Membrane Is Permeable to Small Molecules", Molecular Biology of the Cell, 2004, 447-455, 15.
Liu, et al., "Disulfide bond structures of IgC molecules", mAbs, 2012, 17-23, 4:1.
Lyons et al., "Site-specific attachment to recombinant antibodies via introduced surface cysteine residues", Protein Engineering, 1990, 703-708, 3(8).
Margittai, et al., "Oxidative Protein Folding in the Secretory Pathway and Redox Signaling Across Compartments and Cells", Traffic, 2011, 1-8, 12.
Margittai, et al., "Oxidative folding in the endoplasmic reticulum: Towards a multiple oxidant hypothesis?", FEBS Letters, 2010, 2995-2998, 584.
Meister, et al., "Glutathione", Ann. Rev. Biochem, 1983, 711-760, 52.
Pollard, et al., "Ero1p: A Novel and Ubiquitous Protein with an Essential Role in Oxidative Protein Folding in the Endoplasmic Reticulum", Molecular Cell, 171-182, 1.
Schwartz, et al., "Structural Basis for the Function of the Beta Subunit of the Eukaryotic Signal Recognition Particle Receptor", Cell, 2003, 793-803, 112.
Sevier et al., "Conservation and Diversity of the Cellular Disulfide Bond Formation Pathways", Antioxidants and Redox Signaling, 2006, 797-811, 8.
Sevier, "New insights into oxidative folding", J. Cell Biol., 2010, 757-758, 188(6).
Shen, et al., "Conjugation site modulates the in vivo stability and therapeutic activity of antibody-drug conjugates", Nature Biotechnology, 2012, 184-191, 30(2).
Spens, et al. "Defined Protein and Animal Component-Free NSO Fed-Batch Culture", Biotechnology and Bioengineering, 2007, 1183-1194, 98(6).
Stimmel, et al., "Site-specific Conjugation on Serine-Cysteine Variant Monoclonal Antibodies*", Journal of Biological Chemistry, 2000, 30445-30450, 275, 39.
Sutherland, et al., "SGN-CD33A: a novel CD33-targeting antibody-drug conjugate using a pyrrolobenzodiazepine dimer active in models of drug-resistant AML", Blood, 2013, 1455-1463, 122(8).
Trexler-Schmidt et al., "Identification and Prevention of Antibody Disulfide Bond Reduction During Cell Culture Manufacturing", Biotechnology and Bioengineering, 2010, 452-461, 106(3).
Tsai, et al., "Protein Disulfide Isomerase Acts as a Redox-Dependent Chaperone to Unfold Cholera Toxin", Cell, 2001, 937-948, 104.
Tu et al., "Biochemical Basis of Oxidative Protein Folding in the Endoplasmic Reticulum", Science, 2000, 1571-1574, 290.
Voynov, et al., "Design and Application of Antibody Cysteine Variants", Bioconjugate Chem., 2010, 385-392, 21.
Yoshimori, et al., "Protein Disulfid-isomerase in Rat Exocrine Pancreatic Cells Is Exported from the Endoplasmic reticulum Despite Possessing the Retention Signal*", The Journal of Biological Chemistry, 1990, 15984-15990, 265 (26).
Zhang, et al., "Free Sulfhydryl in Recombinant Monoclonal Antibodies", Biotechnol. Prog., 2002, 509-513, 18.
Zheng, et al., "Conformations of IgE Bound to Its Receptor FcRI and in Solution", Biochemistry, 1991, 9125-9132, 30.
Zhong, et al., "Pyroglutamate and O-Linked Glycan Determine Functional Production of Anti-IL 17A and Anti-IL22 Peptide-Antibody Bispecific Genetic Fusions", The Journal of Biological Chemistry, 1409-1419, 288(2).
International Search Report dated Feb. 17, 2017 for International Application No. PCT/IB2016/054789, filed Aug. 9, 2016.
Written Opinion of the International Searching Authority for International Application No. PCT/IB2016/054789, filed Aug. 9, 2016.
Wikipedia contributors, "TCEP Fact Sheet", Wikipedia, The Free Encyclopedia, 2 pages.
"TCEP Fact Sheet", Uptima, 3 pages.

* cited by examiner

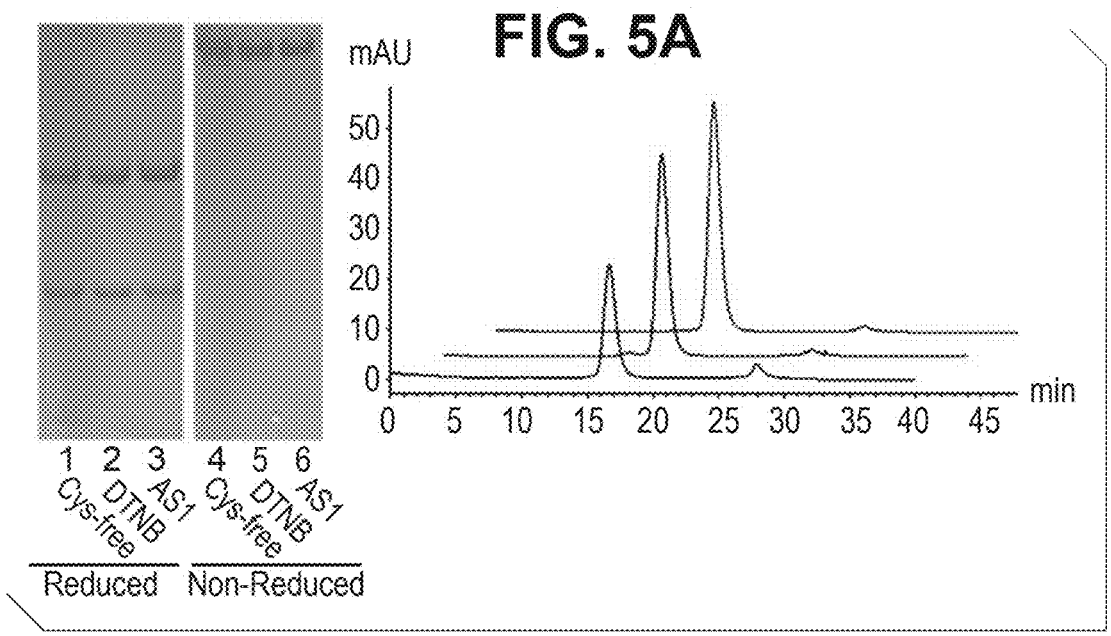
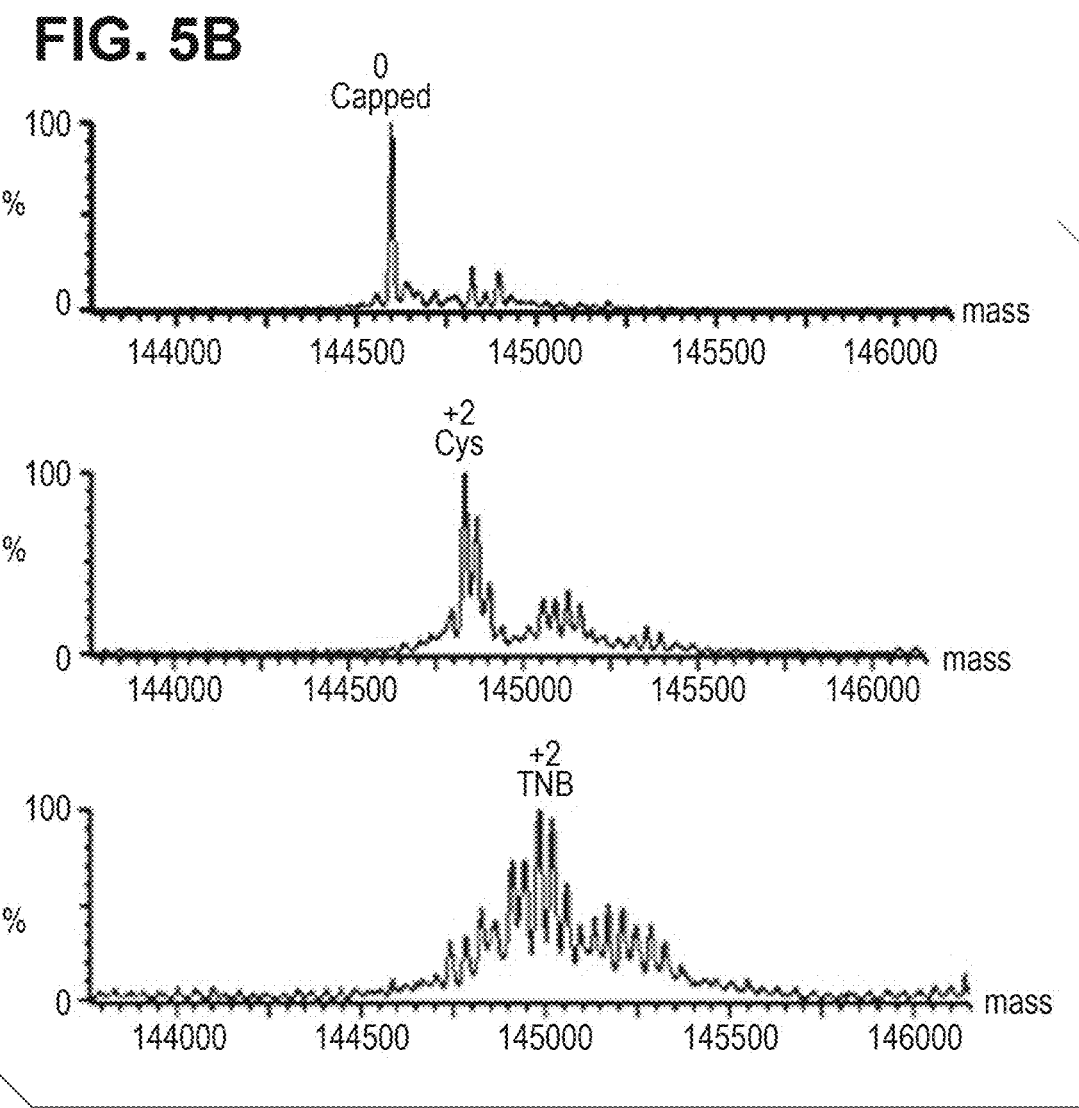

CAPPED AND UNCAPPED ANTIBODY CYSTEINES, AND THEIR USE IN ANTIBODY-DRUG CONJUGATION

CROSS-REFERENCE TO RELATED APPLICATIONS

This Application is the national stage filing under 35 U.S.C. 371 of Patent Cooperation Treaty Patent Application No. PCT/IB2016/054789, filed Aug. 9, 2016, which claims the benefit of U.S. Provisional Application No. 62/204,005 filed on Aug. 12, 2015, the contents of each of which are hereby incorporated by reference in their entirety.

FIELD OF THE INVENTION

The invention is based on the discovery that the capping status of cysteine residues on antibodies can be modified in live cells. Thus the invention relates to antibody production process in mammalian cells in which engineered unpaired cysteine residues are post-translationally modified and capped with particular chemical entities, which capped antibodies are well suited to further site-specific conjugation steps to form antibody-drug conjugates (ADCs) or protein drug conjugates. The invention further relates to ADCs produced using these capped antibodies, in particular ADCs formed by the selective reduction of the capped antibodies' cysteine residues which avoids the reduction of inter-chain disulfides and thus eliminates the need for a (re)oxidation step prior to conjugation. The invention further relates to novel nitrobenzoate-capped antibodies which allow for selective reduction with tris (3-sulfonatophenyl) phosphine (TSPP) or related agents for direct conjugation, and therefore eliminates treatments of interchain disulfide reduction-reoxidation steps. The invention also relates to engineering novel Cys-cappings, consisting of chemical handles such as aldehyde/azide/alkyne biorthogonal groups, which permit additional drug conjugation chemistry. The invention further relates to uncapped antibodies produced by cells in low cysteine, cystine and glutathione media, and ADCs produced via direct conjugation to these uncapped antibodies.

BACKGROUND OF THE INVENTION

ADCs have emerged as a promising class of targeted therapeutics with significant potential to improve clinical efficacy and tolerability over antibody therapy or traditional chemotherapy. Clinically useful ADCs are capable of antigen-specific delivery of highly potent cytotoxic drugs to tumor cells. Monoclonal antibody moiety of ADCs can specifically recognize cell surface antigens which are substantially more elevated in tumor cells than healthy cells, thus decreasing non-specific uptake and increasing specific update of conjugated drugs by tumor cells. Recent clinical data have led to the commercialization of two FDA-approved ADCs products, including brentuximab vedotin: an anti-CD30 monoclonal antibody conjugate, and Ado-trastuzumab emtansine: an anti-HER2 monoclonal antibody conjugate. A third marketed ADC is gemtuzumab ozogamicin, an anti-CD33 monoclonal antibody conjugate, is commercially available in Japan.

The approach by which drugs attach to an antibody (i.e., conjugation) is an important aspect of ADC development. All three referenced commercial ADC products utilize conventional non-specific conjugation method. Brentuximab vedotin is produced by the modification of native cysteine side chain thiols in solvent-exposed disulfides, whereas ado-trastuzumab emtansine and gemtuzumab ozogamicin are made via modification of surface lysine side chain amines. These non-specific conjugation methods have resulted in heterogeneous ADC mixtures.

In order to improve therapeutic index and pharmacokinetics of ADCs, cysteine-based site-specific ADCs have recently been developed to generate more homogeneous drug products with greater control over drug attachment sites. Unpaired cysteine residues have long been introduced into proteins for site-specific labeling and drug conjugation. See: Lyons et al., Protein Eng. 3, 703-708 (1990); Zheng et al., Biochemistry, 30, 9125-9132 (1991); Stimmel, et al., J. Biol. Chem. 275, 30445-30450 (2000); Junutula et al., Nat. Biotechnol., 26, 925-932 (2008); Voynov et al., Bioconjug. Chem. 21, 385-392 (2010); and Shen et al., Nat. Biotechnol., 30, 184-189 (2012). These engineered cysteine residues are typically located on the surface of a protein, and do not alter protein structure and function. It has been recently shown that cysteine-based site-specific ADCs possess improved therapeutic index and reduced toxicity over conventional Cys conjugates and Lys conjugates. See: Junutula et al., Nat. Biotechnol., 26, 925-932 (2008); Junutula et al., Clin. Cancer Res. 16, 4769-47788 (2010); Shen et al., Nat. Biotechnol., 30, 184-189 (2012); and Kung et al., Blood 122, 1455-1463 (2013).

Cysteine-based site-specific ADCs, however, introduce complexity into the drug conjugation process. When produced in mammalian cells, the thiol group(s) of unpaired cysteine residues of cysteine mutant antibody has been found to form disulfides with other cysteines (cysteinylation) or glutathione (glutathionylation) (Junutula, Raab et al. 2008, Chen, Nguyen et al. 2009). These post-translational modifications are called cysteine-capping or Cys-capping. This cysteine-capping creates thiol linked blocking groups which prevent or inhibit conjugation, and thus prior to drug conjugation the thiol group needs to be regenerated through a partial reduction step with reducing agents. Since this treatment also reduces the antibody inter-chain disulfides (also known as "paired" cycteines) those reduced antibody inter-chain disulfides must then be reformed. This is accomplished in a re-oxidation process including dialyzing out reducing agents, cysteine or glutathione, and treating with oxidation reagents. This reduction and reoxidation potentially introduces disulfide shuffling (also called disulfide scrambling, see dashed oval below for illustration) and twisting on the antibody. A twisted antibody can adversely affect protein folding and protein quality, and also cause issues such as poorer PK for resulting ADCs. This phenomenon is shown in FIG. 17.

The underlining mechanism for these "natural" cysteinylation and glutathionylation cappings are unclear. Since both modifications involve forming disulfide bond, it has long been speculated that these modifications may take place in the lumen of endoplasmic reticulum (ER) where disulfide bond formation occurs. It is well known that ER lumen is more oxidized than cytosol (Hwang, Sinskey et al. 1992), due to a highly-conserved oxidation molecular pathway (Frand, Cuozzo et al. 2000, Sevier and Kaiser 2006). Flavin-containing membrane-protein Ero1 (Frand and Kaiser 1998, Pollard, Travers et al. 1998) exploits oxidation power of oxygen to introduce disulfide bonds within itself, then transfers disulfide bond to protein disulfide isomerase (PDI) which can pass it onto extracellular proteins (Tu, Ho-Schleyer et al. 2000). Alternative Ero1-independent oxidation pathways, such as quiescin sulphydryl oxidase/Erv superfamily and vitamin K epoxide reductase, also contribute to disulfide bond formation in mammalian cells (Margittai and Banhegyi 2010, Sevier 2010). GSH is present in ER lumen due to either a transporter (Hwang, Sinskey et al. 1992, Banhegyi, Lusini et al. 1999) or pores (Le Gall, Neuhof et al. 2004) in the membrane. Cys is also presumably present due to a transport activity (Hwang, Sinskey et al. 1992). Therefore an oxidative ER lumen plus the presence of GSH and Cys has made ER lumen a reasonable place for glutathionylation or cysteinylation. However, no conclusive evidence exists in supporting this hypothesis.

SUMMARY OF THE INVENTION

The invention relates to antibody production process in mammalian cells in which engineered unpaired cysteine residues are post-translationally modified and capped with particular chemical entities, which capped antibodies are well suited to further site-specific conjugation steps to form antibody-drug conjugates (ADCs). The invention further relates to ADCs produced using these capped antibodies, in particular ADCs formed by the selective reduction of the capped antibodies' cysteine residues which avoids the reduction of inter-chain disulfides and thus eliminates the need for a (re)oxidation step prior to conjugation. The invention further relates to novel nitrobenzoate-capped antibodies, in particular 5-thio-2-nitrobenzoic acid (TNB)-capped antibodies, which type of capped antibodies allow for selective reduction with tris (3-sulfonatophenyl) phosphine (TSPP) or related or similar-acting reducing agents for direct conjugation, and therefore eliminates treatments of interchain disulfide reduction-reoxidation steps. The invention also relates to engineering novel cysteine-cappings, consisting of chemical handles such as aldehyde/azide/alkyne biorthogonal groups, which permit additional drug conjugation chemistry.

Optimizing culture medium allows the generation of cysteine-mutant antibody with diverse capping statuses, including cysteinylated, glutathionylated, uncapped, or nitrobenzoate capped antibodies. Novel nitrobenzoate-capped antibodies in particular allow for selective reduction with TSPP followed by direct conjugation, eliminating the necessity of using harsh treatments of inter-chain disulfide reduction/reoxidation steps. Key features of the conjugation process as provided in certain embodiments of the present invention are shown in FIG. 18 where antibody that might ordinarily be capped by a cysteine (cysteinylated), and thus conjugated using the above-described reduction and oxidation steps, is capped instead with TNB. The TNB capping is removed, and simultaneously conjugation is accomplished, via selective reduction (e.g., using TSPP) as shown in FIG. 19.
Because reoxidation is avoided, the process disclosed allows the antibody to maintain its original folding and remain intact. Thus the present invention thus represents a novel method which profoundly improves and simplifies the drug conjugation process for cysteine-based site-specific ADCs.

Thus in certain embodiments of the invention cysteine mutant antibodies are capped with nitrothiobenzoate when dithionitrobenzoate is added to the medium. In this embodiment Ellman's reagent, also known as 5,5'-dithiobis-(2-nitrobeoic acid) and DTNB, acts to add thionitrobenzoate (TNB) to an antibody expressed by a cell line, for example a CHO cell line. This is followed by antibody purification, and can produce a majority of the protein species with thionitrobenzoate capping. See Invention Example 1.

In another embodiment of the invention TNB capping of antibodies does not decrease thermal stability, for instance as measured by DSC, such that cysteinylated, uncapped, and TNB-capped antibody behaved nearly identically. See invention Example 2.

In yet another embodiment of the invention TNB-capped antibody is selectively reduced with TSPP. In this embodiment, free thiol groups generated in this process allow for direct drug conjugation without the interchain reduction and reoxidation steps, which in turn speeds up the in vitro manipulation process. See Example 3.

As noted herein, another embodiment of the invention includes the formation of engineered cysteine cappings comprising chemical "handles" other than TNB or similar labile moieties useful for additional types of drug conjugation chemistry. These handles are appended to the antibody by adding novel alkylating chemical spacers into the culture medium. The alkylating chemical spacers contain chemical handles such as aldehydes, ketones, azides, and alkynes. In the case of ketones and aldehydes, these chemical handles can react with aminooxy nucleophiles or hydrazide for additional conjugation chemistry, forming oxime/hydrazone products. In the case of azides and alkynes, these chemical handles can permit cycloaddition conjugation. Additional alkylating chemical spacers includes functional domain of Biotin, which allows specific tight non-covalent interaction between Strepavidin and Biotin. See Example 4 which discusses the chemical handle maleimido trioxa-4-formyl benzamide (MTFB), dibenzocyclooctyl-polyethylene maleimide (DBCO-PEG4-Maleimide), and Maleimide-PEG2-Biotin (MPB).

Thus we have additionally demonstrated that by adding alkylating chemical spacers into culture medium, novel Cys-cappings consisting of chemical handles such as aldehyde group can be engineered. These novel cappings can provide chemical handles for additional drug conjugation chemistry, in part as depicted in FIG. 20

| Chemical Functionality | Reactive Group "X" | Capped mAb (X-mAb) |
|---|---|---|
| Haloacetyl & Alkyl halide derivatives | R—C(=O)—CH₂—I | R—C(=O)—CH₂—S-mAb |
| Maleimides | R—CH₂—N(maleimide) | R—CH₂—N(succinimide)—S-mAb |

| Chemical Functionality | Reactive Group "X" | Capped mAb (X-mAb) |
|---|---|---|
| Aziridines | R—[aziridine ring with NH] | R—CH(NH$_2$)—CH$_2$—S-mAb |
| Acryloyl Derivatives | R—CH=CH$_2$ | R—CH$_2$—CH$_2$—S-mAb |
| Arylating Agents | R—CH$_2$—(phenyl-F) | R—CH$_2$—(phenyl-S-mAb) |
| Thiol-Disulfide Exchange Reagents | R—S—S—R$_1$ | R—S—S—mAb |
| Vinylsulfone Derivatives | R—S(O)$_2$—CH=CH$_2$ | R—S(O)$_2$—CH$_2$—CH$_2$—S-mAb |

R-alkyl, aryl, heteroaryl, azide, alkyne, aldehyde, ketone, cytotoxic payloads (auristatins, calicheamicins, maytansinoids, spliceostatins, CPI/CTI dimers, etc)

A further embodiment includes the generation of fully uncapped cysteine mutant antibody via HEK293 transient or CHO stable expression in culture media having zero or low levels of cysteine-, cystine- and glutathione. See Examples 5 and 6.

In this application, recitation or discussion of culture media having zero or low levels of cysteine-, cystine- and glutathione- refers to media which have: 0-5 mM cysteine, preferably 0-1 mM cysteine, and most preferably 0.2 mM cysteine; and 0-5 mM glutathione, preferably 0-1 mM glutathione, and most preferably 0.2 mM glutathione. Media with these characteristic component levels are available commercially or can readily be prepared from commercially available media using conventional techniques. Occasionally these media having zero or low level of cysteine-, cystine- and glutathione- are referred to a "triple-free" media, or "triple-low" media.

As used herein, the term "alkyl" by itself or as part of another term refers to a straight chain or branched, saturated hydrocarbon having the indicated number of carbon atoms (e.g., "C1-C6" alkyl refer to an alkyl group having from 1 to 6 carbon atoms). Alkyl groups typically comprise from 1 to 20 carbon atoms, preferably from 1 to 6 carbon atoms, and more preferably from 1 to 4 carbon atoms. When the number of carbon atoms is not indicated, the alkyl group has from 1 to 8, or from 1 to 6, carbon atoms. Representative straight chain C1-C8 alkyls include, but are not limited to, methyl, ethyl, n-propyl, n-butyl, n-pentyl, n-hexyl, n-heptyl and n-octyl; while branched C1-C8 alkyls include, but are not limited to, -isopropyl, -sec-butyl, -isobutyl, -tent-butyl, -isopentyl, and -2-methylbutyl; unsaturated C2-C8 alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl. Reference to "alkyl" herein refers to unsubstituted and substituted moieties as described above.

As used herein, the term "aryl" by itself or an part of another term, means a substituted or unsubstituted monovalent carbocyclic aromatic hydrocarbon radical of 5-20, preferably 5-14 or 6-14, carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Heteroaryl" refers to a monovalent substituted or unsubstituted aromatic monocyclic, bicyclic or tricyclic ring system having from 2 to 10, 2 to 14, or 2-20 carbon atoms, preferably 3 to 8, carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. Heteroaryls may be monocyclic, bicyclic, or tricyclic ring systems. Representative heteroaryls include but are not limited to triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. Heteroaryls are optionally substituted.

As used herein the term "predetermined" refers to a chemical component that is selected by the precticioner of the invention, as opposed to a chemical component that happens to be present. Thus a "predetermined capping moiety" is a capping moiety that has been selected by the practicioner of the invention for placement on (i.e., covalently bonding to) the cysteine residue(s) of an antibody. A predetermined capping moiety is typically a component selected for addition to a culture medium that results in the presence of a particular and desired cap on an antibody. A predetermined capping moiety is not found in a general purpose culture medium.

A further embodiment includes the direct conjugation of a payload or linker-payload species to an uncapped cysteine mutant antibody.

It is notable that production of fully uncapped solvent-exposed unpaired Cys in antibody in mammalian cells is unusual, since only very low percentage of free cysteine residues has been previously detected in recombinant antibodies of IgG1, IgG2, and IgG4 (Zhang and Czupryn 2002). Canonical Cys residues for a normal IgG are presumably disulfide-bonded. Low level of free Cys is likely due to two sources: One source is the degradation of interchain disulfide bonds between heavy chains or between heavy chain and light chain. Cys residues forming inter-chain disulfide bonds are susceptible to reduction (Liu and May 2012), because they are highly solvent-exposed. Under basic conditions, disulfide bonds can be decomposed into dehydroalanine and persulfide which can revert back to Cys (Florence 1980). The other source is the incomplete formation of intrachain disulfide bonds during the biosynthesis. Intrachain Cys and disulfide bonds are buried within the anti-parallel β-sheet structures and not solvent-exposed. Non-canonical germline Cys, which is not present in the antibody of this study, are known to exist in antibody variable region. Its frequency in human germline is relatively rare, ranging from 6%-10% (Ehrenmann, Kaas et al. 2010, Buchanan, Clementel et al. 2013). Several reports (Kroon, Baldwin-Ferro et al. 1992, Johnson, Oliver et al. 1997, Gadgil, Bondarenko et al. 2006, Banks, Gadgil et al. 2008, Buchanan, Clementel et al. 2013) indicate that these non-canonical Cys have little effect on protein stability and aggregation. Some of these non-cannoical Cys are found solvent-exposed and cysteinylated (Banks, Gadgil et al. 2008, Buchanan, Clementel et al. 2013). Cysteinylation of these non-canonical Cys likely occurs outside mammalian cells, according to the finding of this study.

It appears that the thiol susceptibility depends on not only extrinsic factors such as oxidative environment but also intrinsic factors such as solvent accessibility and local Cys environment. Cys location at region of Fab, Fc, heavy chain, or light chain is not a factor affecting cysteinylation modification (Banks, Gadgil et al. 2008, Junutula, Raab et al. 2008, Chen, Nguyen et al. 2009, Buchanan, Clementel et al. 2013). The biological consequence of cysteinylation or glutathionylation is unclear. A number of proteins such as tyrosine phosphatases and molecular chaperones, contain redox-sensitive Cys (Georgiou 2002, Barford 2004). For antibody, removal of cysteinylation from a non-canonical Cys doesn't affect protein secondary structure, but apparently improves protein tertiary or quaternary structure, by reducing aggregation and increasing the melting temperatures (Banks, Gadgil et al. 2008). For Fc Cys in this study, cysteinylation has no effect at all on protein structural stability.

Novel Cellular Mechanism Uncovered: Cys-Capping of Unpaired Surface Cysteine Likely Occurs Outside Mammalian Cells-Based on the data from this study, a hypothetic model for Cys-capping modifications is proposed (FIG. 7). Antibody heavy and light chain polypeptides are translocated into ER lumen through Sec61 complex (Schwartz and Blobel 2003). Native disulfide bonds are formed through PDI protein family with oxidation power from Ero1 pathways or other oxidative sources. Incorrect disulfide bonds are reduced by GSH which is generated from cytosolic glutathione reductase (Chakravarthi, Jessop et al. 2006) and imported through membrane transporter (Hwang, Sinskey et al. 1992, Banhegyi, Lusini et al. 1999, Le Gall, Neuhof et al. 2004). Fully assembled Cys mutant antibody remains uncapped and is eventually secreted into culture medium. Ctn and GSH in the culture medium form disulfide bond with free Cys of antibody through disulfide exchange, followed by oxidation of dissolved oxygen in the medium.

The fact that fully uncapped Cys can be generated in mammalian cells might have revealed some interesting physiological redox statuses about the ER lumen. Firstly, the ER lumen is significantly less oxidized than extracellular space. This is consistent with the notion that proper disulfide formation requires both oxidation and reduction reactions in the ER lumen. Native and non-native disulfides are transiently formed and reduced in order to attain a correct conformation. It has been proposed that a precise equilibrium between oxidation and reduction reactions in ER is important for these covalent links remaining dynamic until protein folding is completed. Either an overoxidizing ER, stabilizing non-native bonds, or a reducing ER, preventing disulfide formation, can trigger ER stress responses (Margittai and Sitia 2011). Ero1 and other oxidative pathways contribute to the oxidation power for disulfide formation (Frand, Cuozzo et al. 2000, Sevier and Kaiser 2006, Margittai and Banhegyi 2010, Sevier 2010), making ER lumen more oxidized than cytosol (Hwang, Sinskey et al. 1992). At the same time, the reduced form of GSH generated by cytosolic GSH reductase can be imported into ER lumen to provide reduction power (Jessop and Bulleid 2004, Chakravarthi, Jessop et al. 2006, Gomez, Vinson et al. 2010). Yeast cells can survive without GSH synthesizing pathway, suggesting that yeast's ER lumen is more oxidized than mammalian ER. Since yeast is a unique cellular organism, it is possible that fewer and simpler extracelluar proteins with disulfide bonds are needed to carry out less complicated cellular functions than those of mammalian cells. In addition, a less oxidized ER is further supported by the finding that PDI can reduce misfolded proteins in ER for retrotranslocation for degradation (Kopito and Sitia 2000), unfold cholera-toxin A1 chain for cytosol transport (Tsai, Rodighiero et al. 2001), and serve as reductase when exported to cell surface (Yoshimori, Semba et al. 1990, Jordan and Gibbins 2006).

The second revelation about ER lumen is that free GSH or Cys in the ER lumen, and free Cys residue of a protein, are poor substrates of PDI for forming disulfide bond together. Disulfide bond formation of extracellular proteins is catalyzed by PDI and oxidoreductase family members, whose disulfide bond is transferred from Ero1. Since no disulfide bond is formed between GSH/Cys and the engineered Cys of the antibody in the ER, they are not a substrate of oxidoreductases, even though GSH can reduce oxidized PDI (Chakravarthi, Jessop et al. 2006). It has been reported that a major fraction of ER-located GSH were found to be in mixed disulfide with ER protein (Bass, Ruddock et al. 2004). It is possible that the ER proteins forming mixed disulfides with GSH are PDI and other oxidoreductases. It is worthy of mentioning that besides cysteinylation and glutathionylation, a third type of capping has been identified as an extra light chain forming disulfide bond with the engineered Cys (Gomez, Vinson et al. 2010). The venue for this modification is likely to be ER lumen, as the triple light chain formation was found affected by intracellular GSH production and mRNA ratio between LC and HC.

It has long been unknown why capping percentage varies lot-to-lot (Banks, Gadgil et al. 2008, Junutula, Raab et al. 2008, Chen, Nguyen et al. 2009, Gomez, Vinson et al. 2010, Buchanan, Clementel et al. 2013). Our data indicates that this is due to insufficient Cys/Ctn in the medium which can be affected by cell growth and medium preparation. It is interesting to note that glutathionylated materials were not detected in HEK293 transient culture or short term culture of stable CHO. This is consistent with the fact that GSH concentration in typical mammalian culture medium is very low. On other hand, cytosol contains about 2-10 mM GSH (Meister and Anderson 1983). Glutathionylated materials can be detected in the stable CHO 12-day-culture materials (unpublished data), suggesting that GSH source is likely from cell lysis. Indeed, it has been reported that GSH concentration in the culture medium gradually increased along with the longer culture days and can go nearly 10-fold higher up to 200 µM (Gomez, Vinson et al. 2010). In this study, adding excess GSH or Ctn into culture can produce fully glutathionylated or cysteinylated Cys mutant antibody. It has been previously reported that glutathionylation of purified Cys antibody species can be effectively removed and exchanged with cysteinylation in vitro by using Cys/Ctn redox pair (Chen, Nguyen et al. 2009). Removing cysteinylaton with GSH and generating glutathionylation in vitro haven't yet been reported.

In certain embodiments of the invention there is provided method of bonding a predetermined capping moiety onto one or more unpaired cysteine residues on an antibody, said method comprising the step of: growing an antibody-expressing cell line in a culture medium containing said predetermined capping moiety, or a precursor of said predetermined capping moiety, wherein said cell line expresses said antibody, and wherein said predetermined capping moiety is attached by a covalent bond to at least one of said unpaired cysteine residues on said expressed antibody. The capping moiety may be one selected from the group consisting of 5-thio-2-nitrobenzoic acid (TNB), 2-mercaptopyridine, dithiodipyridine (DTDP), 4-thiobenzoic acid, 2-thiobenzoic acid, 4-thiobenzenesulfonic acid, 2-thiobenzenesulfonic acid, methyl sulfonate (Ms), p-toluenesulfonate (Ts) and trifluoromethanesulfonate (Tf), but other capping moieties are possible.

Such other capping moieties include so-called chemical handle capping moieties, as noted above, such as maleimido trioxa-4-formyl benzamide (MTFB) and more generally, linked azides and alkynes (which facilitate additional click chemistry), linked aldehydes and ketones (which facilitate additional oxime chemistry), linked haloacetyls (which facilitate thiol and amine chemistry), and linked maleimides (which facilitate additional thiol chemistry). The addition linking chemistry may be performed as described herein and also according to known techniques.

The invention also provides for a method of producing an antibody drug conjugate (ADC) or a protein conjugate comprising the steps: (a) producing a capped antibody in a cell culture, wherein one or more unpaired cysteine residues on said antibody are covalently bonded through sulfur bonds to one or more predetermined capping moieties; (b) exposing said capped antibody to a reducing agent capable of removing said capping moieties from said antibody without reducing antibody inter-chain sulfur bonds; and (c) without introducing an oxidizing agent, conjugating one or more reduced sulfur bonds on said antibody to a payload via a linking moiety. The aforementioned method of producing ADCs may be performed where the capping moiety is selected from the group consisting of 5-thio-2-nitrobenzoic acid (TNB), 2-mercaptopyridine and dithiodipyridine (DTDP). Capping with 5-thio-2-nitrobenzoic acid (TNB) is of particular interest.

Such capping typically occurs, followed by a selective reduction at unpaired cysteine residues.

The payload used in the above method is most often an auristatin, a spliceostatin, a calicheamicin or a dimer comprising one or more CBI, CPI and CTI monomer. Where it is an auristatin is may be selected from (2-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide); (2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide); (2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide, trifluoroacetic acid salt); (2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide); (2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide); (2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt); monomethyl dolastatin 10; (N-methylvaline-valine-dolaisoleuine-dolaproine-norephedrine); and (N-methylvaline-valine-dolaisoleuine-dolaproine-phenylalanine).

The linker used in the above method(s) is often mc or mcvcPABC, but many other linkers are within the scope of the invention, including those described in, e.g., WO15/110935. As used herein, "PABC" refers to p aminobenzyloxycarbonyl and moieties derived therefrom, for instance the structure:

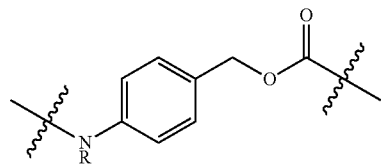

or variants thereof. "VC" or "vc" refers to the peptide valine-citrulline. "MC" or "mc" refers to:

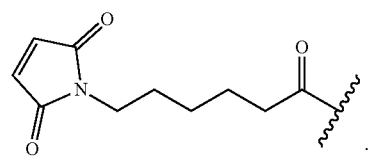 [SMILES: *C(=O)CCCCCN1C(=O)C=CC1=O]

As used herein, "mcvcPABC" refers to the linker:

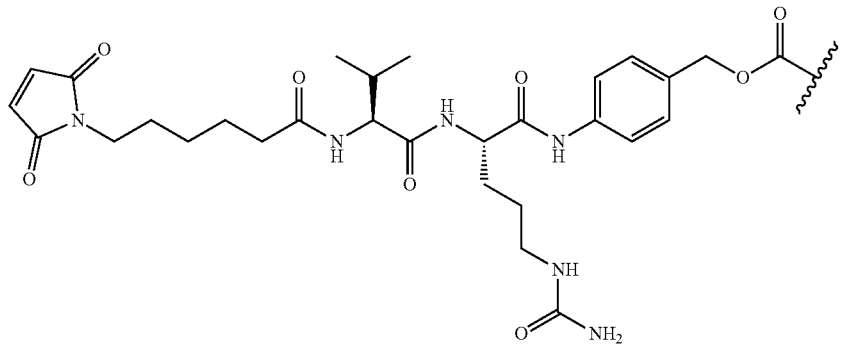 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

In certain embodiments, the reducing agent used in the above method is typically of the formula:

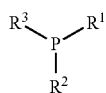

or $R^4$—S—H, where each of $R^1$, $R^2$, $R^3$ and $R^4$ are independently selected from the group consisting of $(C_1-C_6)$ alkyl, $(C_5-C_7)$aryl and $(C_5-C_7)$heteroaryl, wherein each of $R^1$, $R^2$, $R^3$ and $R^4$ is independently optionally substituted with one or more substituent selected from $SO_3Na$, COOH, OH, OMe, $NO_2$ and $NH_2$.

Often the reducing agent is tris (3-sulfophenyl) phosphine (TSPP):

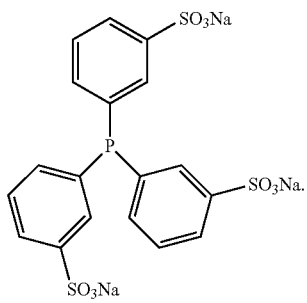

Embodiments of the invention include those in which the capping moiety TNB is appended to the antibody using di-TNB, also known as Ellman's reagent:

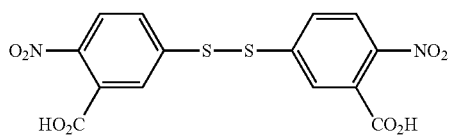

to produce the capped antibody in cell culture.

Further, embodiments of the invention include a method of producing an antibody comprising one or more uncapped unpaired cysteines. Uncapped unpaired cysteines are defined as cysteine residues with exposed thiol side chains. These free thiol groups are not forming any covalent or non-covalent bonds with any other chemicals, thus they are reactive to chemical conjugation. A diagram of uncapped cysteine residues in an antibody is: depicted in FIG. 21.

This method comprises the steps of: (a) growing an antibody-expressing cell in a low cysteine, low cystine and low glutathione culture medium, and (b) collecting expressed uncapped antibody. In this method, the culture medium typically comprises less than 5 mM, less than 1 mM or less than 0.2 mM cysteine, less than 5 mM, less than 1 mM or less than 0.2 mM cystine and less than 5 mM, less than 1 mM or less than 0.2 mM glutathione. Also in this method, the cell line may be selected from the group consisting of CHO, HEK293 and NSO, but of course other cell lines are within the scope of the invention.

Additionally, embodiments of the invention include those wherein there is a method of producing an antibody drug conjugate (ADC) or a protein conjugate, said method comprising the steps of: (a) growing an antibody-expressing cell in a low cysteine, low cystine and low glutathione culture medium, (b) collecting expressed antibody comprising one or more uncapped unpaired cysteines, and (c) conjugating a linker-payload to said collected antibody.

Similarly, the invention includes methods of producing an antibody drug conjugate (ADC) or a protein conjugate comprising the step of conjugating a linker-payload to an isolated antibody comprising one or more uncapped, unpaired cysteines.

DESCRIPTION OF THE FIGURES

FIG. 1.

FIG. 2. Excess GSH or cystine added to the culture medium results in generation of fully glutathionylated or cysteinylated species.

FIG. 3. Fully uncapped cysteine mutant antibody is generated by HEK293 transient expression in low cysteine-, cystine-, and glutathione ("triple-low") medium.

FIG. 4. Fully uncapped cysteine mutant antibody is generated by stable CHO expression in triple-low (low cysteine, low cystine and low glutathione) medium.

FIG. 5. Cysteine mutant antibody is further capped with nitrothiobenzoate (TNB) when dithionitrobenzoate (DTNB, also called Ellman's reagent) is added to the medium. FIG. 5A: SDS-PAGE analysis and SEC analysis of cysteine mutant antibody expressed in stable CHO-DUKX in CD-CHO medium (Thermo-Fischer) (herein, CD-CHO medium refers either to commercially available CD-CHO media or equivalent proprietary media formulations) CD-CHO plus 0.5 mM DTNB, and the triple-low medium. FIG. 5B: Mass spec analysis of Cys mutant antibody as shown in FIG. 5A.

FIG. 9. TNB-capped antibody produces 90% DAR2 ADC with TSPP reduction/conjugation.

FIG. 10. TNB-Capped Herc-K290C/K334C produces 90% DAR4 ADC with TSPP reduction/conjugation.

FIG. 12. Production of MFTB-capped HAB08 L443C in stable CHO cells.

DETAILED DESCRIPTION OF THE INVENTION

General Procedures

Figure 1A:
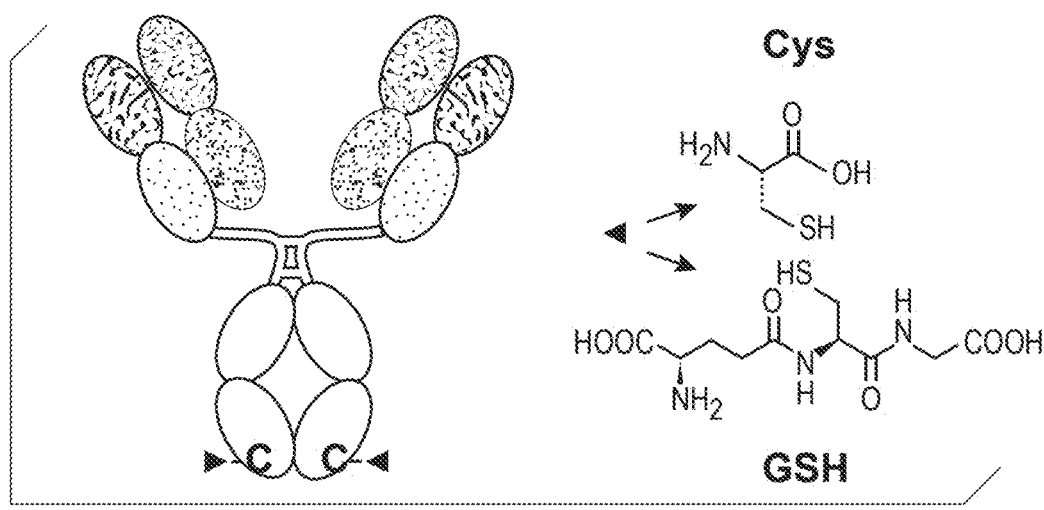
FIG. 1A: Schematic diagram of cysteinylation and glutathionylation of antibody with engineered surface Cys mutation at Fc region.

Cell Culture, Transfections, and Cell Line Development:

Mammalian cell lines were grown and maintained in a humidified incubator with 5% or 7% $CO_2$ at 37° C. CHO cells and HEK293F cells [American Type Culture Collection (ATCC), Manassas, Va.] were cultured in FreeStyle™ 293 expression medium (Invitrogen, Grand Island, N.Y.). A large-scale transient HEK293 transfection process as described in (Zhong, Kieras et al., J. Biol. Chem. 288(2): 1490-1419 (2013)) was used for antibody production. For stable transfection, CHO-DUKX cells were grown in Minimum Essential Medium Eagle Alpha Modification (Sigma-Aldrich, M0644) alpha mediums supplemented with adenosine (10 mg/L), deoxyadenosine (10 mg/L), and thymidine (10 mg/L). The CHO-DUKX cells were transfected with DNAs encoding a cysteine mutant recombinant antibody protein and subjected to selection with 100 nM methotrexate and 1 mg/ml G418. The stable pools were allowed to undergo selection for 3 weeks and then seeded at 2e5 cells/ml into serum-free suspension at 37° C. Stable CHO-DUKX cells were maintained in alpha medium supplemented with 100 nM methotrexate and 1 mg/ml G418. During production, cells were seeded in CD-CHO medium and conditioned media was harvested at the end of production and cleared by centrifugation prior to purification. The triple-free medium is a Minimum Essential Medium Eagle Alpha Modification (Sigma-Aldrich)-like medium for mammalian cell culture, which does not contain GSH, Cys, and Ctn. This media contains insulin as a growth factor and a polymer (Polyvinyl Alcohol) as a shear protectant.

Protein Purification:

rmpProtein A resin (GE Healthcare, Piscataway, N.J.) was pre-equilibrated with 50 mM Tris (tris(hydroxymethyl)aminomethane), 150 mM NaCl, pH 7.5 (TBS) over night at 4° C. The resin was filtered using a 0.2 PES filter and packed into a column where it was washed with 2 CVs of TBS, 5 CVs of $CaCl_2$, pH 7.5, 3 CVs of 10 mM Tris, 10 mM NaCl, pH 7.5 before the protein was eluted using 100% step of 150 mM Glycine, 40 mM NaCl, pH 3.5. The protein was titrated to pH 3.5 using 2M Glycine, pH 7.2 before adjusting the pH to 7.0 using 2M HEPES, pH 8.0. The protein was dialyzed into PBS (137 mM NaCl, 2.7 mM KCl, 8.1 mM $Na_2HPO_4$, 2.7 mM $KH_2PO_4$, pH 7.2) before being concentrated and loaded onto a Superdex 200 column equilibrated with PBS, pH 7.2. Peak fractions were pooled dialyzed into 20 mM Histidine, 8.5% Sucrose, pH 5.8, and then concentrated to 10 mg/mL using a 50 kDa MWCO centrifugal device.

De-Glycosylation of N-Linked Glycans:

Antibody samples were deglycosylated by adding PNGase F (NE BioLabs, Ipswich, Mass.). The samples were acidified by diluting 1:1 with 0.05% TFA (Sigma-Aldrich, St Louis, Mo.), followed by Liquid Chromatography Mass Spectrometry analysis.

Liquid Chromatography Mass Spectrometry:

Liquid chromatography mass spectrometry (LC-MS) analysis was performed using a Waters Xevo Q-TOF G2 mass spectrometer (Waters, Milford, Mass.) coupled to an Agilent (Santa Clara, Calif.) 1200 capillary HPLC. The deglycosylated samples were separated over a Waters BEH300 C4, 1.7 µm, (1.0×50 mm) column maintained at 80° C. with a flow rate of 65 µl/min. Mobile phase A was water with 0.05% TFA, and mobile phase B was acetonitrile with 0.05% TFA. Proteins are eluted from the column using a gradient: 2% to 20% B in 0.5 min, 20% to 40% B in 6 min, and 40% to 100% B in 4 min. The mass spectrometer was run in positive MS only mode scanning from 800 to 3500 m/z and data was acquired with MassLynx (Waters) 4.1 software. The TOF-MS signal corresponding to the antibody were summarized and deconvoluted using MaxEnt1 (Waters) program. Cysteine, GSH, TNB, or MTFB (maleimido trioxa-4-formyl benzamide) capped species were determined by mass shift (Cys: 119.004 Da, GSH: 305.068 Da, TNB:198.175, MTFB: 503.54 Da).

Differential Scanning Calorimetry (DSC):

Thermal stabilities for the Cys mutant antibody protein were analyzed using MicroCal's capillary DSC system, VP-DSC (Northampton, Mass.). The protein samples at concentration of 0.002 mM in a Histidine sucrose formulation were heated from 10 to 110° C. at a scan rate of 100° C. per hour. The resulting heat capacity was baseline corrected by subtracting against a blank Histidine/sucrose formulation scan and fitted with the non-2 state transitions function using Origin7.0 software from MicroCal (OriginLab Corporation, Northampton, Mass.).

REFERENCE EXAMPLES

The reference examples discussed below by-and-large describe the state of the art highlight features of the art which are improved upon by the invention described in in the Invention Examples.

Figure 1B:
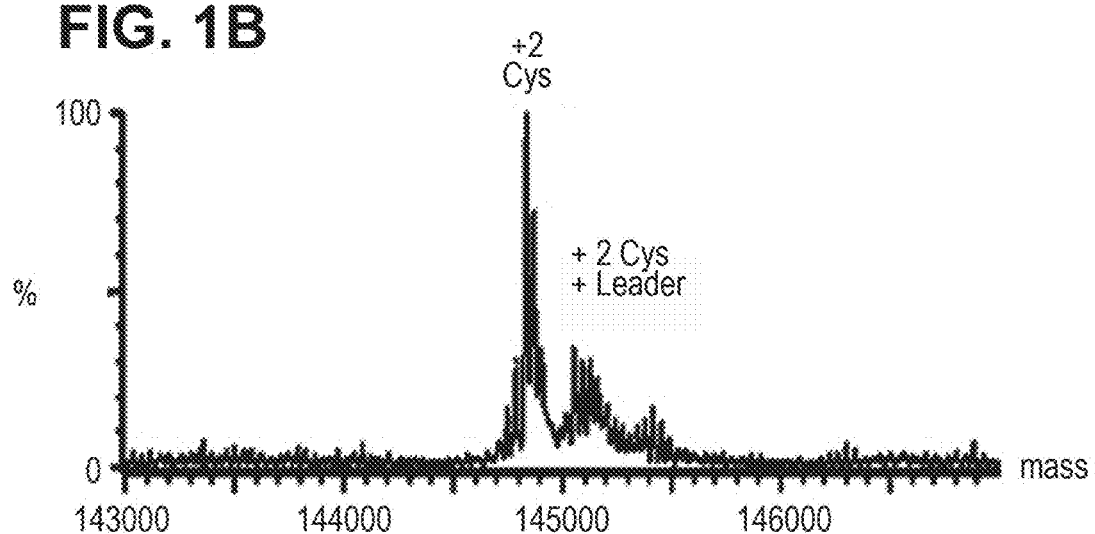
FIG. 1B: Mass spec plot of cysteine mutant antibody expressed in stable CHO-DUKX cells.
Figure 1C:
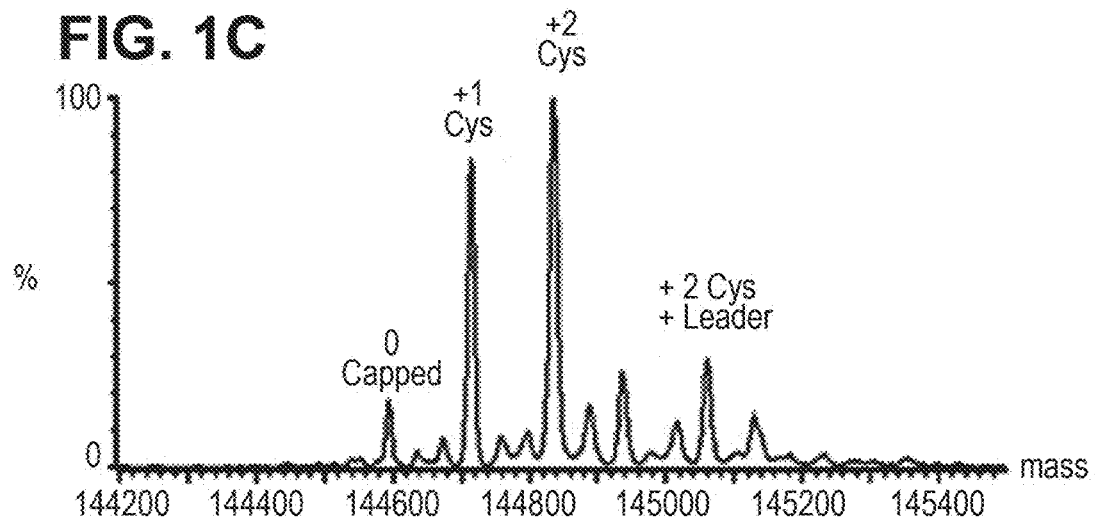
FIG. 1C. Mass spec plot of cysteine mutant antibody expressed in HEK293 transient expression.

Reference Example 1: Detecting Uncapped Cysteine Residues in Cysteine Mutant Antibodies Produced by HEK293 Transient Expression A model antibody HAB08 with a surface leucine modified to cysteine in the CH3 region (FIG. 1A) was investigated. This mutant was found fully cysteinylated when stably expressed in CHO-DUKX cells (see representative mass spec data is shown in FIG. 1B). A very small percentage of gluthionylated species was also detected. When we expressed this mutant by transiently transfecting into HEK293 cells, we surprisingly found that about 10% fully uncapped Cys mutant antibody plus 30% single uncapped materials was detected. The detection of uncapped Cys antibody was consistent while the percentage varied lot-to-lot. Representative mass spec data is shown in FIG. 1C. Very little glutathionylated species were detected in HEK293 transient materials. Protein materials from transient HEK293 and stable CHO both contained small amount of protein species with alternative leader-sequence cleavage.

Figure 2A:
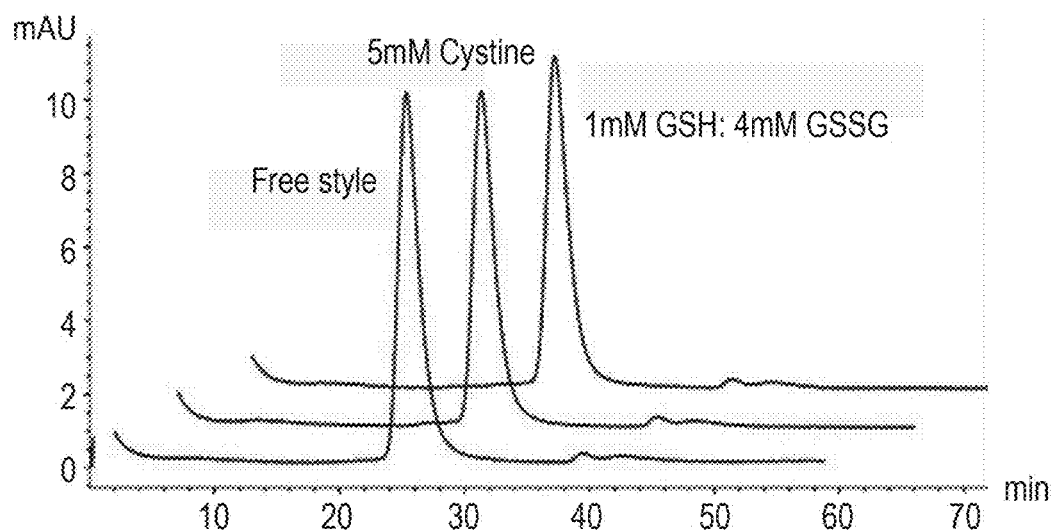
FIG. 2A: SEC analysis of Cys mutant antibody transiently expressed in HEK293 cells with excess cystine or glutathione.
Figure 2B:
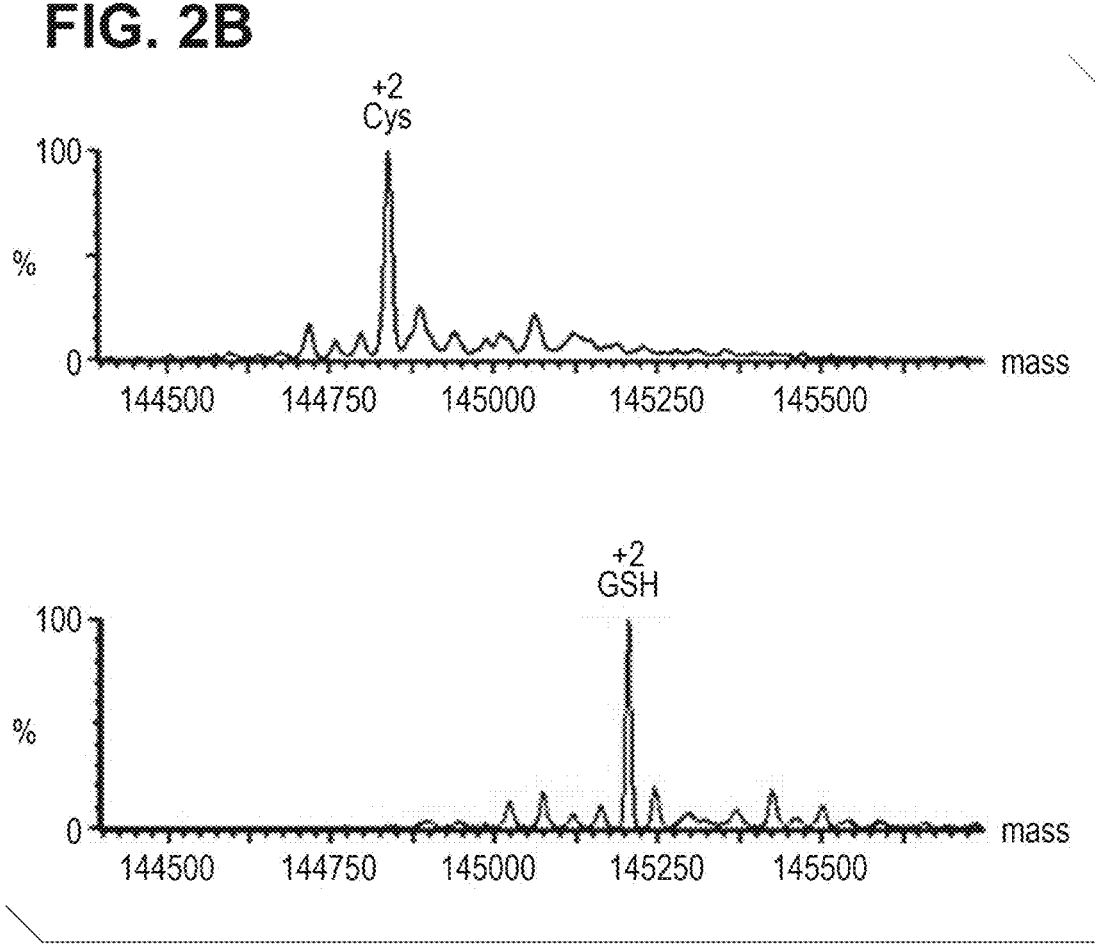
FIG. 2B. Mass spec analysis of cysteine mutant antibodies shown in FIG. 2A.

Reference Example 2: Excess Glutathione or Cystine in Culture Medium Results in Generation of Fully Glutathionylated or Cysteinylated Species As demonstrated in Reference Example 1, cysteine mutant antibodies produced by stable CHO cells were found fully capped with cysteinylation. To determine if the uncapped species detected in HEK293 materials were attributable to the insufficient presence of cysteine and cystine in FreeStyle™ 293 expression medium, excess amount of these molecules were added to the culture medium. HEK293 transient production was therefore conducted in the medium with excess amount of cysteine or glutathione. HEK293 cells were transfected in freestyle medium which was estimated to contain around 1 mM cystine. After the transfection was performed at 24 hr a medium exchange was performed by resuspending transfected cells into either fresh medium or medium containing either additional 5 mM Ctn or 5 mM GSH (reduced:oxidized=1:4). At 96 h, cell viability was measured, conditioned medium was harvested, and antibody was purified. Both culture conditions shared nearly identical cell growth viability (>80%), protein expression level (~30 mg/L), proA elution profile, and protein migration pattern in SDS-PAGE. FIG. 2A shows the data of analytical size-exclusion column (SEC), which indicates nearly identical chromatography with less than 1% protein aggregation. The protein samples were analyzed in mass spec for measuring their capping status, as shown in FIG. 2B. In contrast to the control FreeStyle™ 293 expression medium samples which had un-capped, 1-capped and 2 capped heterogeneous capping species, as shown in FIG. 1C. The protein sample from culture medium with additional 5 mM Ctn was fully Cysteinylated-capped, and the protein sample from culture medium with additional GSH was fully glutathionylated-capped. Thus, by adding sufficient amounts of cysteine or glutathione into the culture medium fully cysteinylated or glutathionylated cysteine mutant antibody was produced.

The Reference Examples above, and the Invention Examples below, demonstrate that cysteine-capping occurs outside of, not within, mammalian cells. This implies cysteine capping with other reagents could be produced if these reagents are added directly into medium during cell culture. Novel capped materials could potentially provide advantages to drug conjugation process.

EXAMPLES

The following Example illustrate important features of the invention.

Example 1: Cysteine Mutant Antibodies are Capped with Nitrothiobenzoate when Dithionitrobenzoate is Added to the Medium Ellman's reagent, 5,5'-dithiobis-(2-nitrobeoic acid) (DTNB) was examined as a capping agent to add thionitrobenzoate (TNB). (DTNB is commonly used for assaying free thiol content in proteins. This reagent cannot disrupt disulfide bond but can react with free Cys. It has been used to treat partially-reduced antibody materials to generate four free Cys for drug conjugation.) A CHO cell line stably expressing the cysteine mutant antibody was grown to 4×10e6/ml in CD-CHO medium, then switched to fresh CD-CHO medium, fresh CD-CHO medium with 0.5 mM DTNB, or the triple-low medium as a control. Cells were cultured in these conditions for 72 hrs, cell viability was measured and conditioned medium was harvested. Cell viability of stable CHO cells in the medium with DTNB dropped to 40%, possibly indicating that DTNB was toxic to CHO cells. The color of the DTNB cell culture turned yellow, suggesting that free thionitrobenzoate was present in the culture and alkylation to cell surface protein occurred. Protein expression in the DTNB-containing medium was also 5-fold lower than those in CD-CHO. Antibody purification from ProA column and protein migration in SDS-PAGE from all three culture conditions materials were nearly identical, as shown in FIG. 5A. All three samples in SEC analysis show monomer species, with very little aggregation. As shown in Table 1, all three capping forms could be concentrated to about 10 mg/ml with less than about 2% aggregation, and the proteins were stable after freeze-thaw treatment.

TABLE 1

Biochemical summary of Cys mutant antibody with different capping statuses.

| Capping status | Protein concentration | Monomer | Freeze-Thaw |
|---|---|---|---|
| Cysteinylated | 10.52 mg/ml | 98.4% | Stable |
| Uncapped | 10.19 mg/ml | 98.0% | Stable |
| TNB-Capped | 12.92 mg/ml | 97.44% | Stable |

As shown in FIG. 5B, the mass spec data indicates that the control CD-CHO medium produced fully cysteinylated (mass increase of 238 Da) and that the triple-low medium generated fully uncapped materials. The DTNB medium produced a majority (>70%) of the protein species with thionitrobenzoate capping (mass increase of ~396 Da). A small percentage of fully cysteinylated species were also present as around 1 mM cystine was present in the medium. DTNB thus was more efficient for cysteine-capping than cystine. Since DTNB is a charged molecule and not membrane permeable, this result provides further evidence showing cysteine capping occurs outside the cell.

Example 2: TNB Capping of Antibodies does not Decrease Thermal Stability

Figure 6:
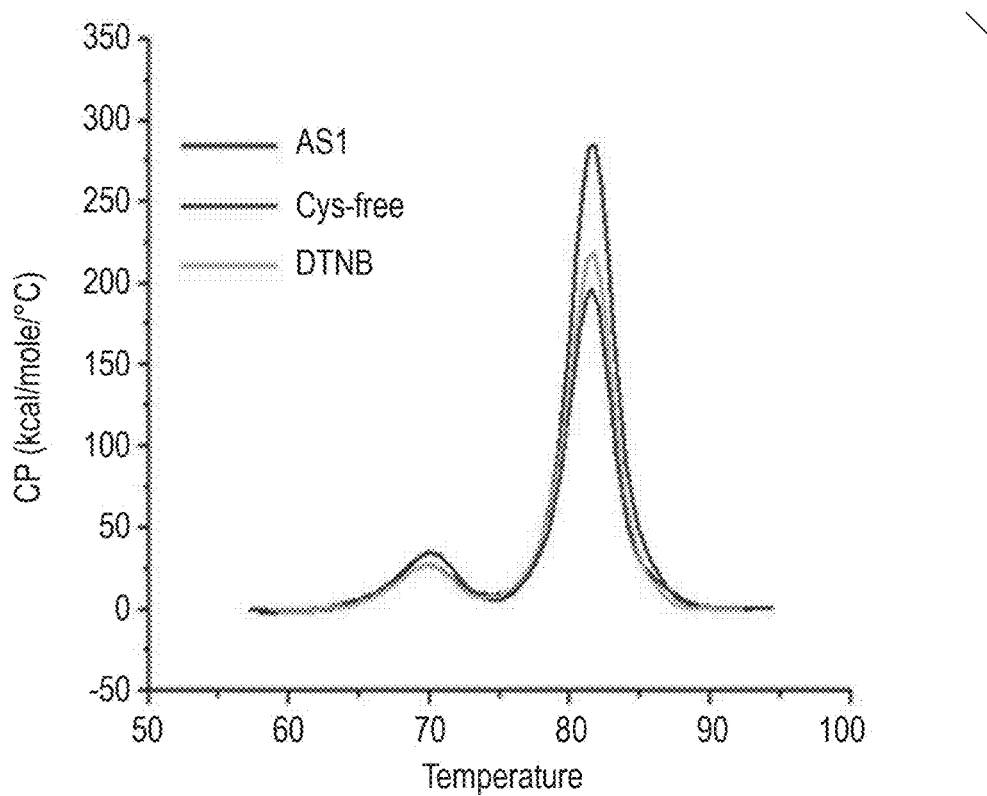
FIG. 6. DSC thermogram comparing the melting temperatures of cysteine mutant antibodies which are cysteinylated, uncapped, and nitrobenzoate-capped, and accompanying data table.
Figure 7:
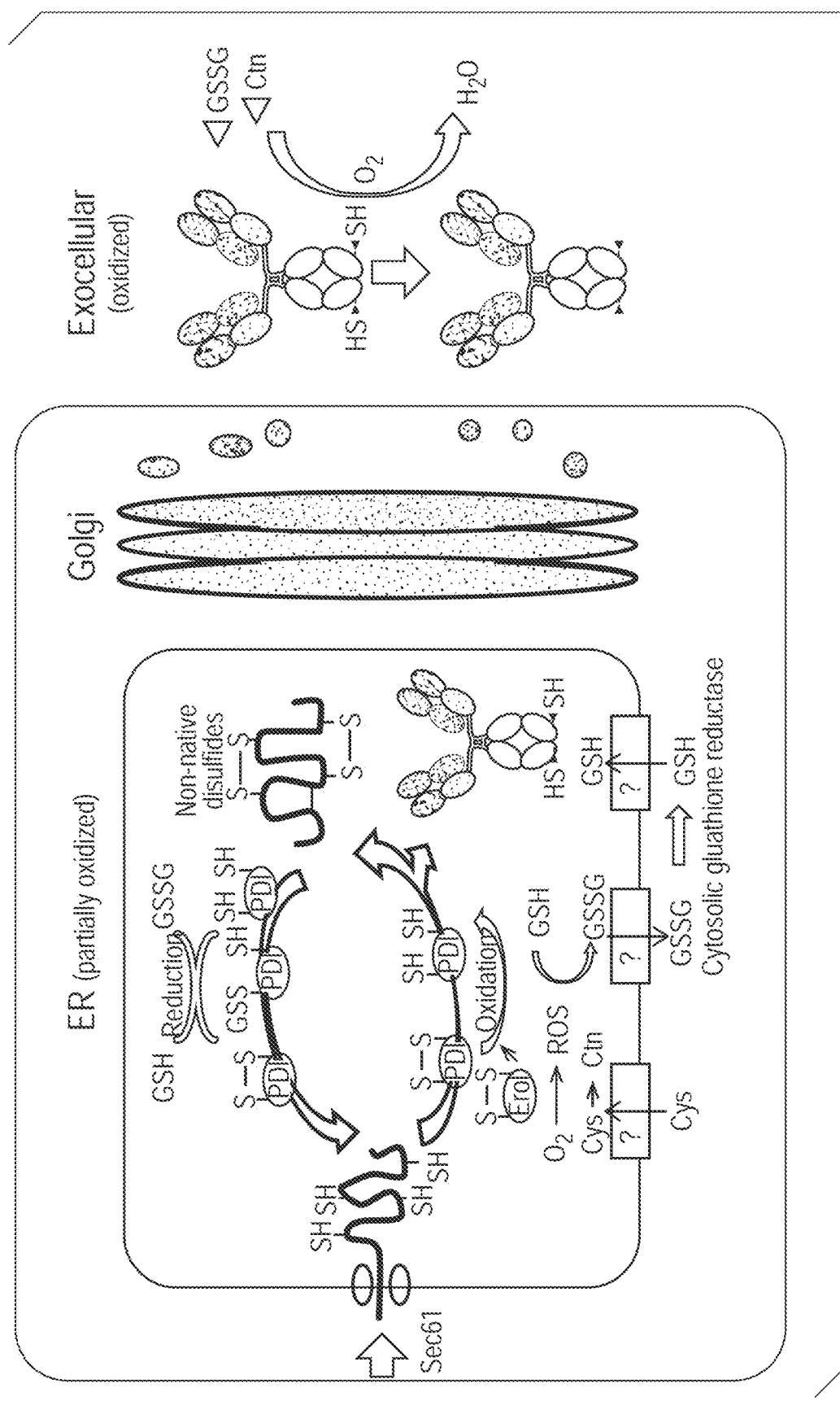
FIG. 7. Understood likely mechanism of cysteinylation and glutathionylation modifications in cysteine mutant antibody in mammalian cells.

The consequences of TNB capping were investigated to determine whether structural changes induced by such capping destabilize the antibody. DSC was employed to monitor thermal stability of the antibody with cysteinylation, uncapped, or thiobenzoate-capped. As shown in FIG. 6, cysteinylated, uncapped, and TNB-capped antibody behaved nearly identically, with Tm1 of over 69° C. In contrast to the cysteinylation in Fab region (Banks, Gadgil et al. 2008) which is known to result in a 6° C. decrease of melting temperature versus the uncapped materials, cysteinylation and nitrobenzoate-capping in the unpaired Cys at the CH3 region do not appear affecting structural stability of the antibody. This is consistent with the observation that antibody with uncapped Cys can be concentrated to 10 mg/ml with little protein aggregation, and contradicts the assumption that a reactive thiol triggers protein oligomerization.

Example 3: Selective Reduction of TNB-Capped Antibody with TSPP

Figure 8:
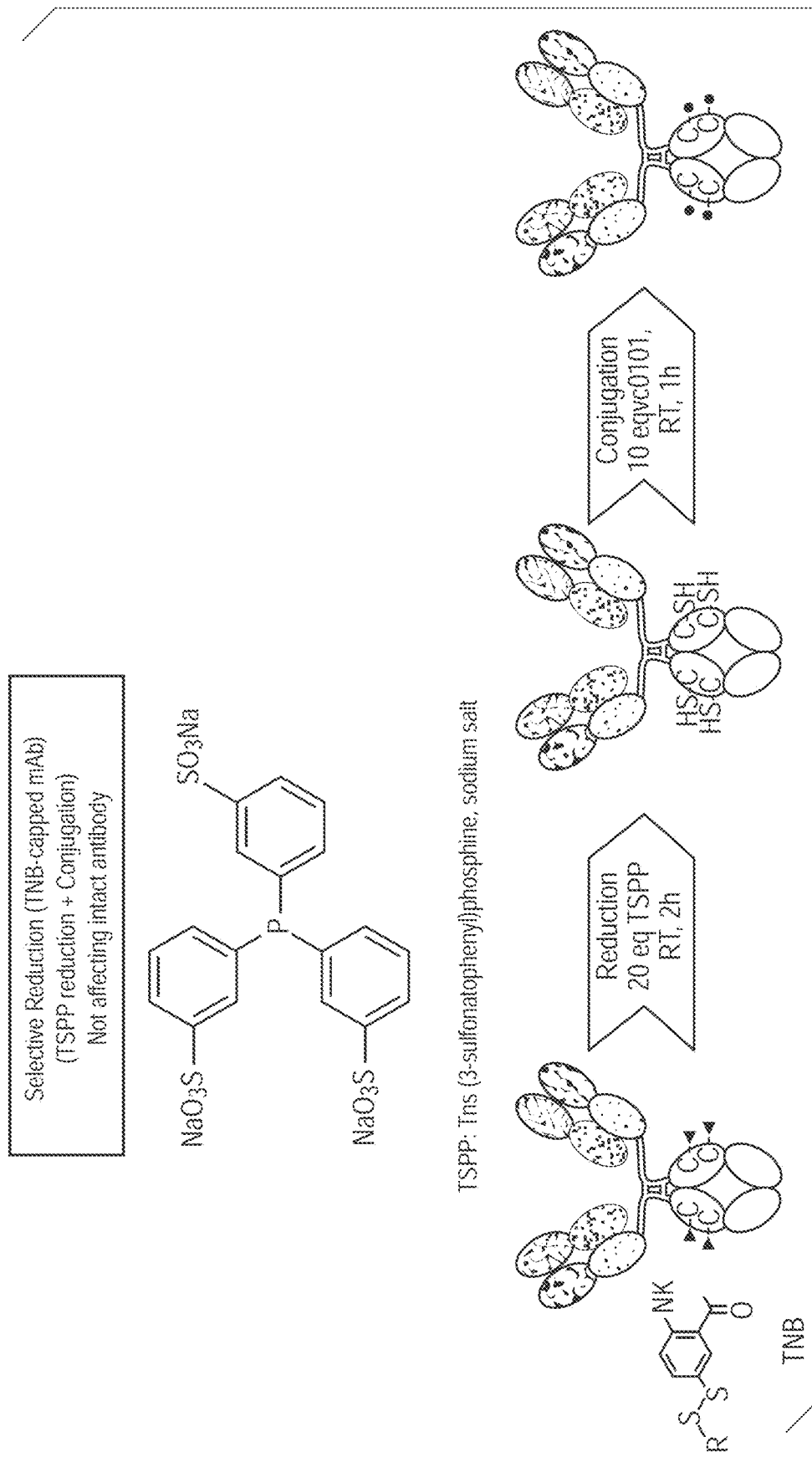
FIG. 8. TSPP selective reduction and direct conjugation eliminates inter-chain disulfide reduction/reoxidation.
Figure 9A:
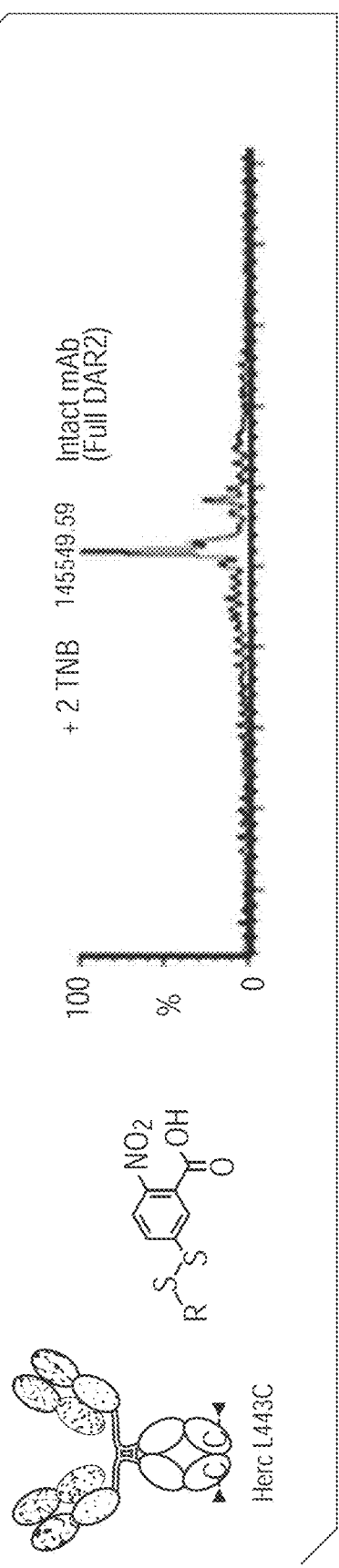
FIG. 9A. Mass spec analysis of cysteine mutant antibody digested with PNGase F for intact antibody of L443C.
Figure 9B:
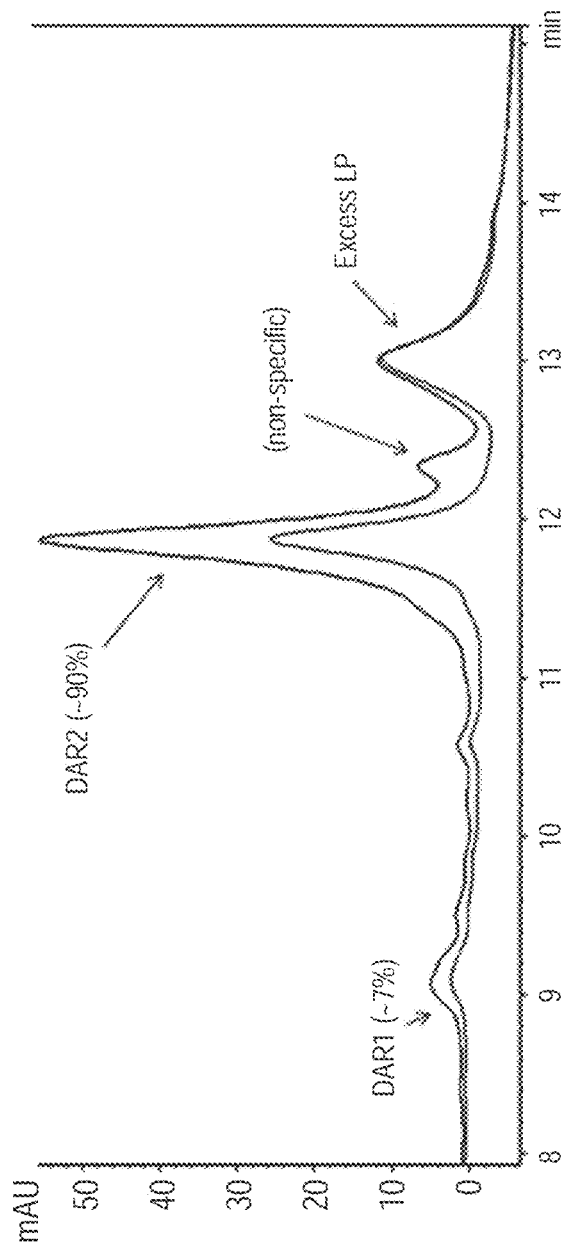
FIG. 9B. TSPP selective reduction and subsequent direct conjugation of mcvc-PABC0101 linker payload.
Figure 10A:
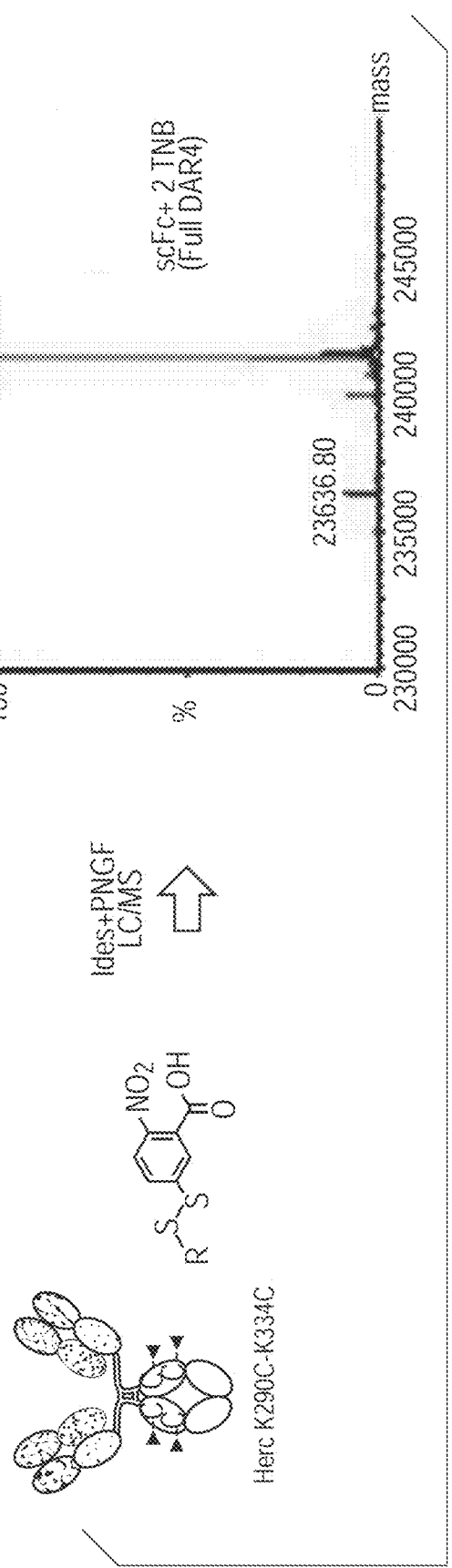
FIG. 10A. Mass spec analysis of cysteine mutant antibody digested with PNGase F and IdeS for Fc region K290C/K334C.
Figure 10B:
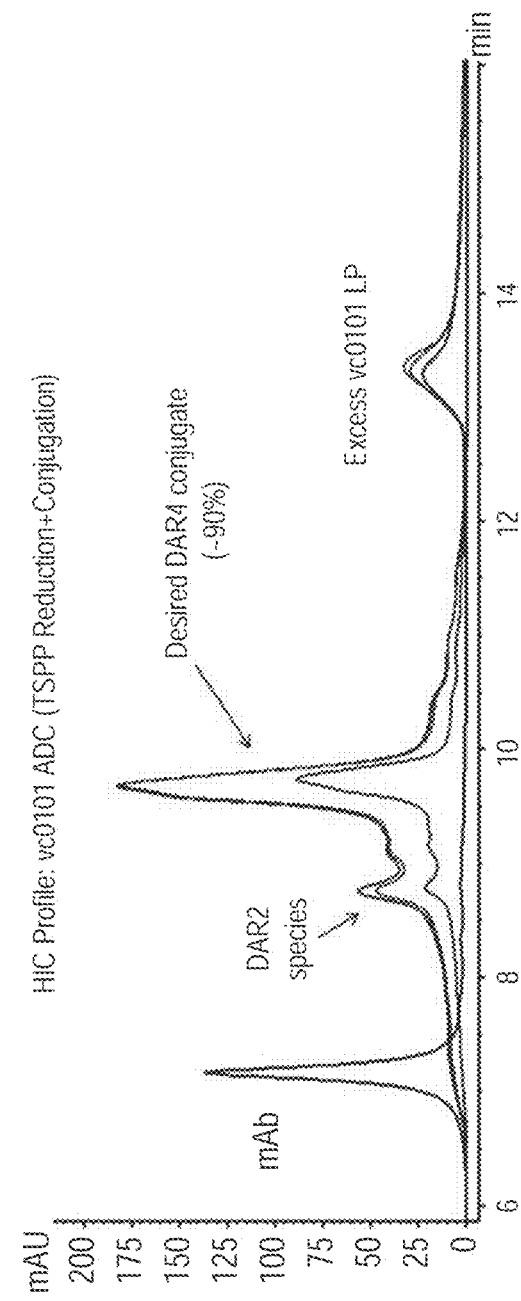
FIG. 10B. TSPP selective reduction and subsequent direct conjugation of mcvcPABC0101 linker payload.

Cysteine mutant antibody capped with TNB is selectively reduced with TSPP (FIG. 8). Free thiol groups generated allow direct drug conjugation without the interchain reduction and reoxidation steps, which speed up the in vitro manipulation process. Further, as shown in FIG. 9A, Herceptin L443C fully capped with TNB (2 cappings per antibody, or DAR2) was generated and analyzed via mass spec. DAR2 TNB-capped antibody was direct-conjugated after TSPP treatment with an efficiency of 90% as analyzed by HIC (FIG. 9B). Similarly, Herceptin K290CK334C fully capped with TNB in the form of 4 cappings per antibody (DAR4) was generated and analyzed via mass spec after IDES and PNGase F digestion (FIG. 10A), and direct-conjugated after TSPP treatment with an efficiency of 90% (FIG. 10B).

As a further example, TNB-capping and conjugation (K290C/K334C) is herein discussed. The TNB-capped conjugation protocol for cysteine mutant conjugation consists of two steps leading to the crude conjugate: selective reduction, and conjugation. In the first step a selective reduction of mutant cysteines, (but not interchain disulfides) is accomplished to achieve the removal of protecting group(s) from mutant cysteine residues. Typically this is done using an excess (~10 equivalents) of a reducing agent such as tris(3-sulfophenyl phosphine) (TSPP) at 25° C. for 2 h. In a specific instance: To 1 mg (6.9 nmol; 7.6 mg/mL in PBS; 131.58 uL) of K290C/K334C antibody in a 0.5 mL eppendorf tube was added 39.2 μg of TSPP (10 equivalents; 69.05 nmol; 50 mM in water; 1.38 μL). The reaction mixture was incubated at 25° C., 2 h.

In a second step the unprotected mutant cysteines are conjugated to linker-payload. Typically an excess (~10 equivalents) of linker-payload is added to reaction and the reaction is done at 25° C. for 1 h to produce the crude conjugate. Thus in a specific instance: To the reaction mixture from step 1 above was added 92.6 μg of mcvc-PABC0101 linker-payload (10 equivalents, 69.05 nmol; 10 mM in dimethylsulfoxide; 6.9 μL). The reaction mixture was incubated at 25° C., 1 h. A hydrophobic interaction chromatography (HIC) assay was used to analyze reaction mixture.

Figure 11:
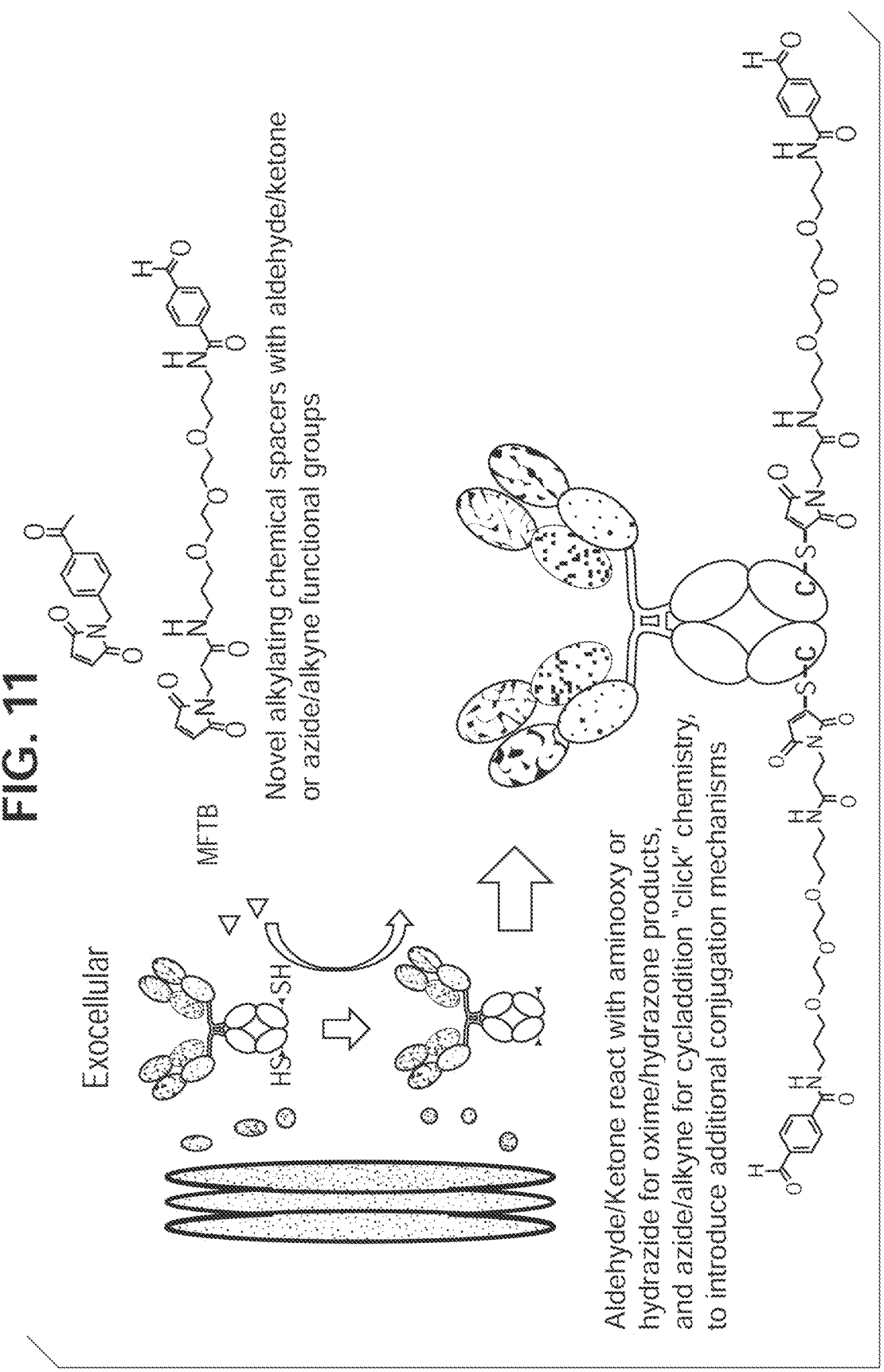
FIG. 11. Production of novel cysteine-capped chemical spacers with new chemical handles other than reactive thiols.

Example 4: Additional Engineered Cysteine Cappings with Chemical Handles for Additional Drug Conjugation Chemistry Another application of the invention is to engineer novel cappings (i.e., other than TNB) by adding novel alkylating chemical spacers into the culture medium. As shown in FIG. 11, these alkylating chemical spacers contain chemical handles such as aldehyde or azide functional groups, which permit additional drug conjugation chemistry. In case of ketone/aldehyde, they can react with aminooxy nucleophiles or hydrazide for additional conjugation chemistry, forming oxime/hydrazone products.

Maleimido trioxa-4-formyl benzamide (MTFB) is a maleimide with a PEG3 linker and 4-formylbenzamide (Solulink Inc, San Diego, Calif.). As shown below, MTFB is an alkylating chemical spacer with an aldehyde group:

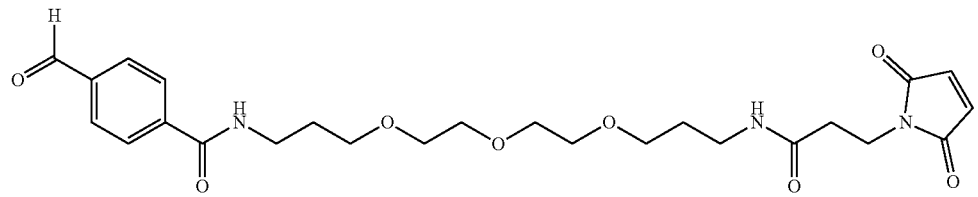 [SMILES: O=Cc1ccc(C(=O)NCCCOCCOCCOCCCNC(=O)CCN2C(=O)C=CC2=O)cc1]

Figure 12A:
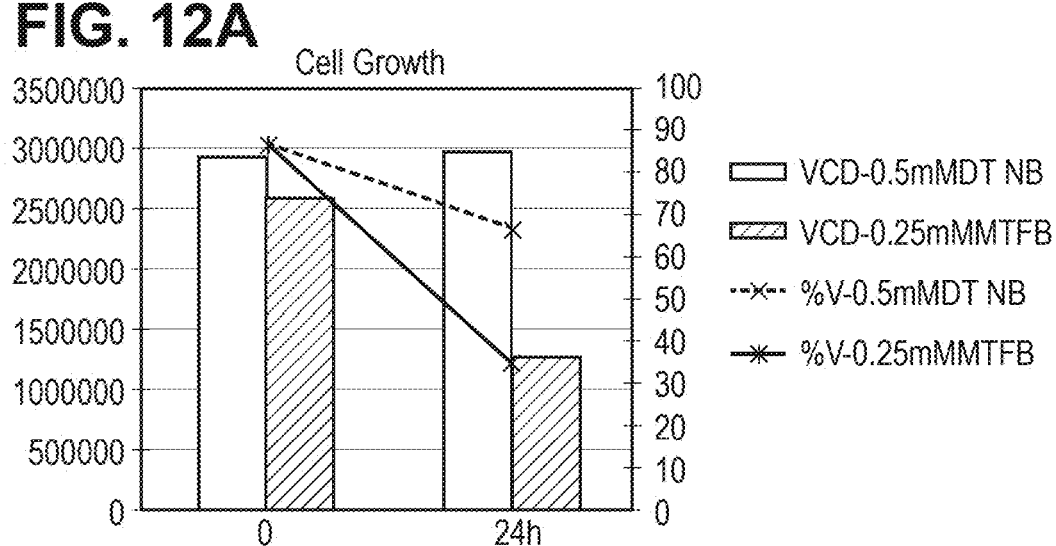
FIG. 12A. Cell count and cell viability of stable CHO cells in the presence of MFTB or DTNB in triple-low medium.
Figure 12B:
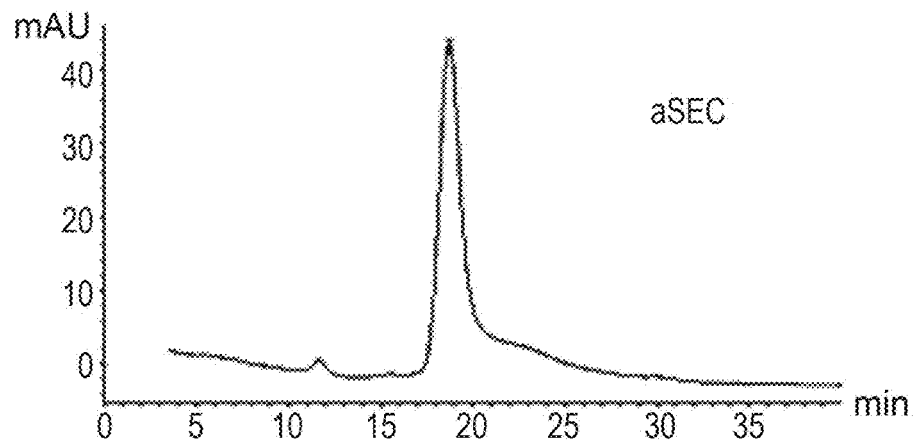
FIG. 12B. SEC analysis of cysteine mutant antibody expressed in stable CHO cells in triple-low medium with MFTB.
Figure 12C:
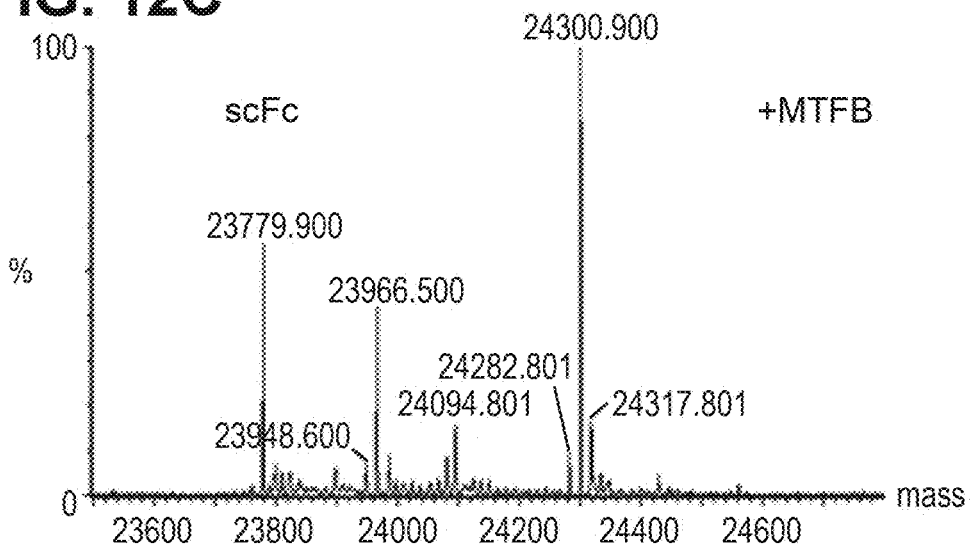
FIG. 12C. Mass spec analysis of cysteine mutant antibody digested with PNGase F for intact antibody of L443C.

As shown in FIG. 12A, CHO-DUKX cells stably expressing antibody HAB08L443C were grown in CD-CHO medium to around 2.5e6 cells/ml at 37° C., then switched triple-low medium (zero or low Cys-, Ctn-, and GSH). 19.8 mM MTFB, dissolved in DMSO, was added to 50 ml cell culture at a final concentration of 0.25 mM for 24 hr. Cell viability was measured and conditioned medium was harvested. Comparing to controlled culture with 0.5 mM DTNB, cell viability and cell counts at the condition with MTFB were significantly lower. Antibody HAB08L443C at such condition was subsequently purified by a 1 ml-ProA column (FIG. 12B). Such antibody was subjected to 2-Part LC/MS study, with first digested with PNGF to remove Fc-glycans and IDES to separate Fab2 from scFc containing 443 Cys. As shown in FIG. 12C, MTFB-capped HAB08 L443C antibody species was produced.

The aldehyde group of MTFB-capped antibody reacts with hydrazines or aminooxy-containing payloads such as aminooxy-PEG3-C2-Amide-MMAD. 10 µM of antibody and payload is incubated in the presence of 100 mM aniline freshly prepared in 0.3M Na phosphate (pH 7.0). The reaction carries on at room temperature for 24 h for forming hydrazone or oxime products. The final conjugated antibody is purified through HIC column.

Alkylating chemical spacers containing chemical handles such as alkyne or azide functional groups permit cycloaddition conjugation. As shown below, Dibenzocyclooctyl-polyethylene maleimide (DBCO-PEG4-Maleimide) is a maleimide with a PEG4 linker and dibenzocyclooctyl (Click Chemistry Tools, Scottsdale, Ariz.). Azido-PEG3-Maleimide is a maleimide with a PEG3 linker and azido domain (Click Chemistry Tools, Scottsdale, Ariz.).

Figure 14:
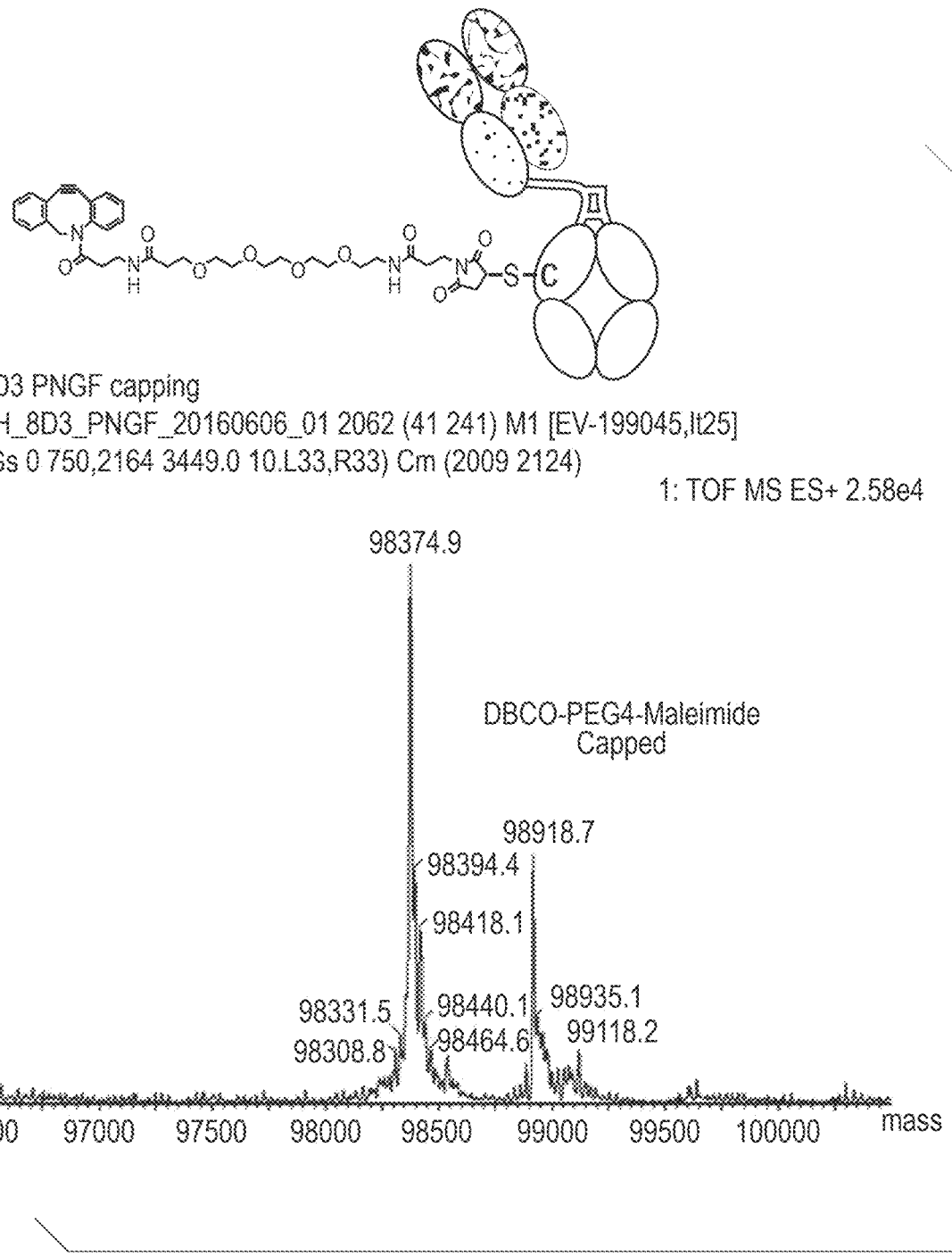
FIG. 14. Production of DBCO-PEG4-Maleimide-capped K290C one-arm antibody 8D3 in transient HEK293 cells. Mass spec analysis of cysteine mutant antibody digested with PNGase F for intact molecule of K290C one-arm antibody 8D3.

To demonstrate that novel Cys-capping with DBCO-PEG4-Maleimide was generated, HEK293F cells were transiently transfected with a one-arm antibody 8D3K290C in 2 L of FreeStyle medium at cell density of 2.0e6 cells/ml at 37° C. At 24 hours post-transfection, HEK293F cells were then switched to triple-low medium (zero or low Cys-, Ctn-, and GSH) for additional 96 hours at 37° C. Conditioned medium was harvested, filtered, and incubated with a final concentration of 0.14 mM DBCO-PEG4-Maleimide from a stock concentration of 29.6 mM dissolved in DMSO for additional 24 hr at 37° C. One-arm antibody 8D3K290C from such conditioned medium was subsequently purified by a 5 ml-ProA column. Such antibody was subjected to LC/MS study, first digested with PNGase F to remove Fc-glycans. As shown in FIG. 14, DBCO-PEG4-Maleimide-capped 8D3K290C antibody species was produced. Similarly, azide-PEG3-Maleimide-capped 8D3K290C was also produced.

For cycloaddition conjugation reaction, 10 µM azido-PEG3-Maleimide-capped antibody in PBS buffer is incubated with 100 µM dibenzocyclooctyl-polyethylene glycol (DBCO-PEG)-MMAF (ACME Bioscience; Palo Alto, Calif.) at room temperature for 16 h. The copper-free click conjugation reaction is stopped by addition of 1 mM sodium azide. Conjugated antibody can be purified by HIC column.

Additional novel Cys-capping examples include alkylating chemical spacers with functional domain of Biotin. This Cys-capping with Biotin allows specific non-covalent interaction between Strepavidin and Biotin for cell imaging and protein labeling. As seen below, Maleimide-PEG2-Biotin (MPB) is a maleimide with a PEG2 linker and a Biotin domain.

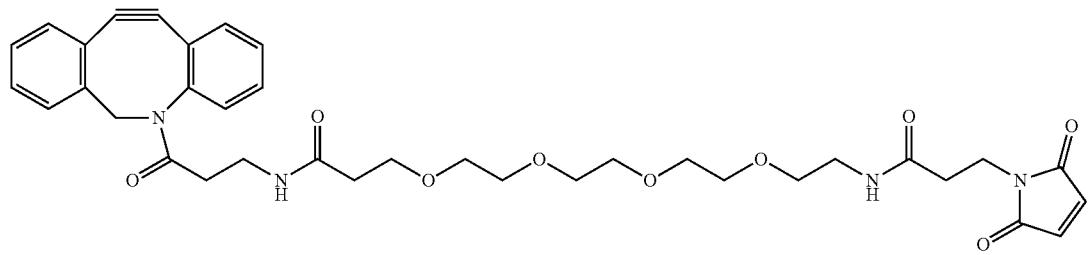

(DBCO-PEG4-Maleimide)

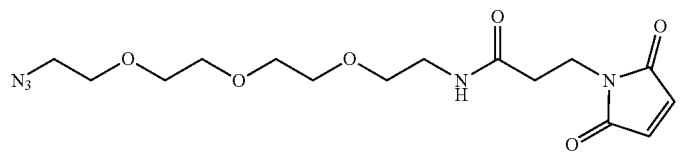

(Azido-PEG3-Maleimide)

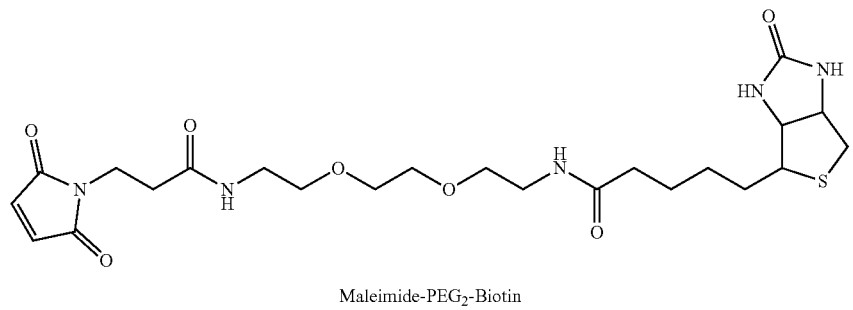 [SMILES: O=C(CCCCC1SCC2NC(=O)NC21)NCCOCCOCCNC(=O)CCN1C(=O)C=CC1=O]

Maleimide-PEG$_2$-Biotin

Figure 15:
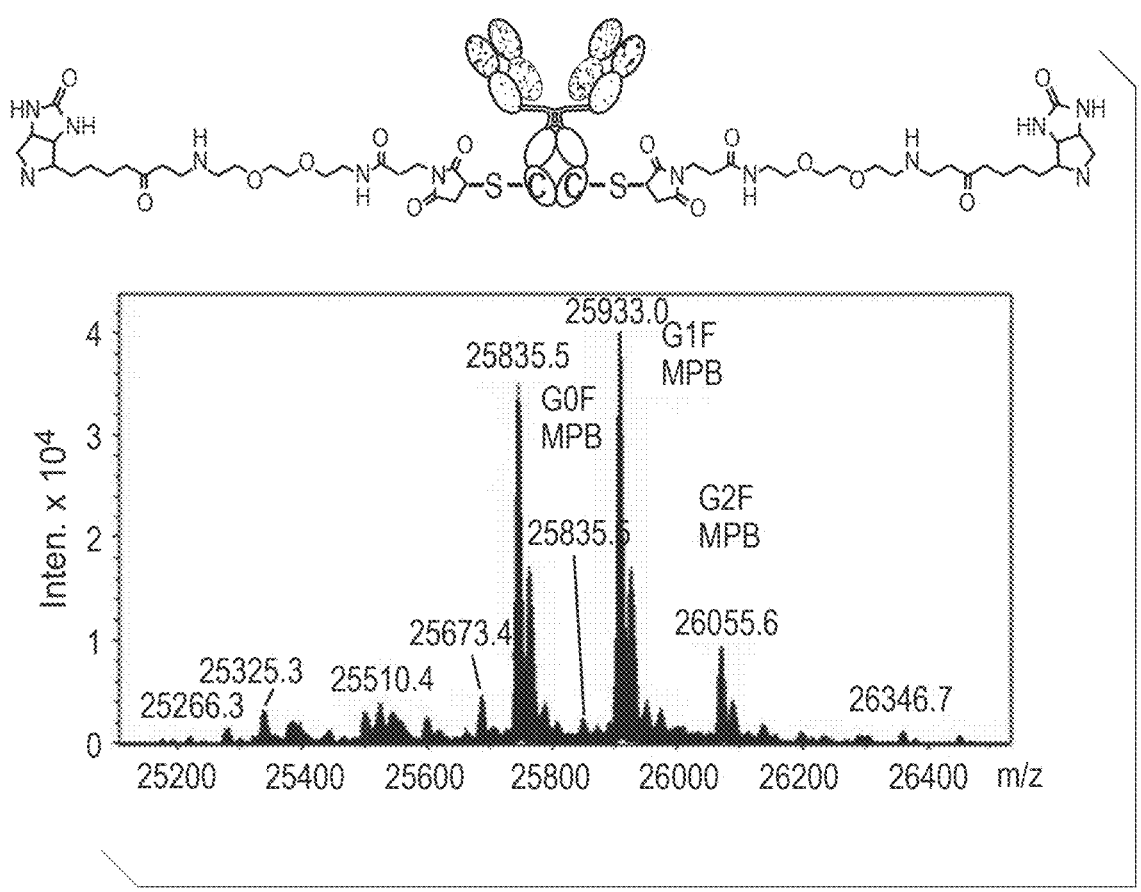
FIG. 15. Production of Maleimide-PEG2-Biotin-capped HAB08 L443C in stable CHO cells. Mass spec analysis of intact antibody of HAB08 L443C.

CHO-DUKX cells stably expressing antibody HAB08L443C were grown in CD-CHO medium to around 2.5e6 cells/ml at 37° C., then switched to a triple-low medium (zero or low Cys-, Ctn-, and GSH). 20 mM Maleimide-PEG2-Biotin was added to 50 ml cell culture at a final concentration of 0.2 mM for 48 hr. Cell viability and cell counts were not affected by MPB-treatment. Antibody HAB08L443C under such culturing condition was subsequently purified by a 1 ml-ProA column and subjected to a 2-Part LC/MS study, digested with both PNGase F to remove Fc-glycans and IDES to separate Fab2 from scFc containing 443 Cys. As shown in FIG. 15, MPB-capped HAB08 L443C antibody species was produced.

Figure 3A:
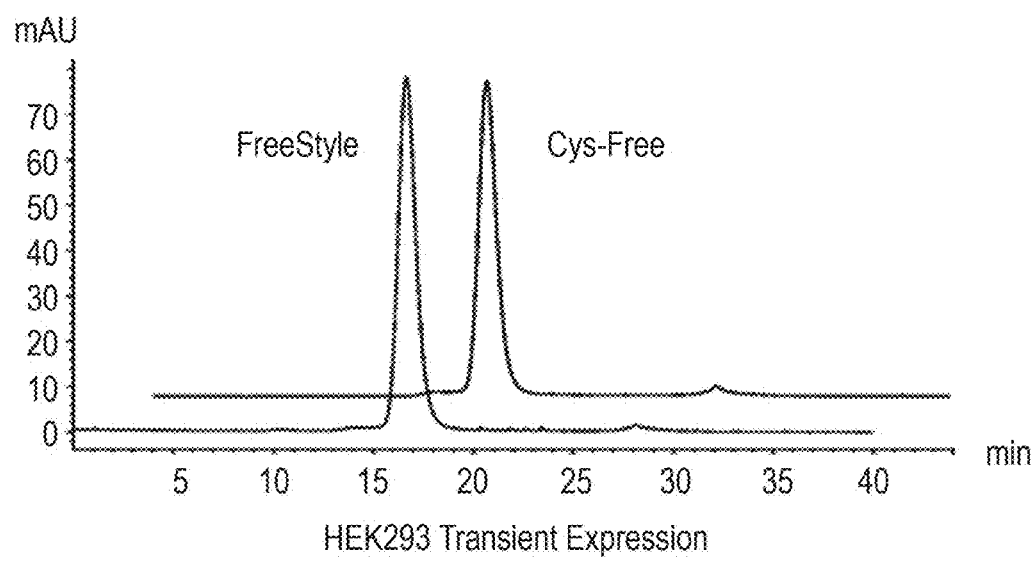
FIG. 3A: SEC analysis of cysteine mutant antibody transiently expressed in HEK293 cells in triple-low medium.
Figure 3B:
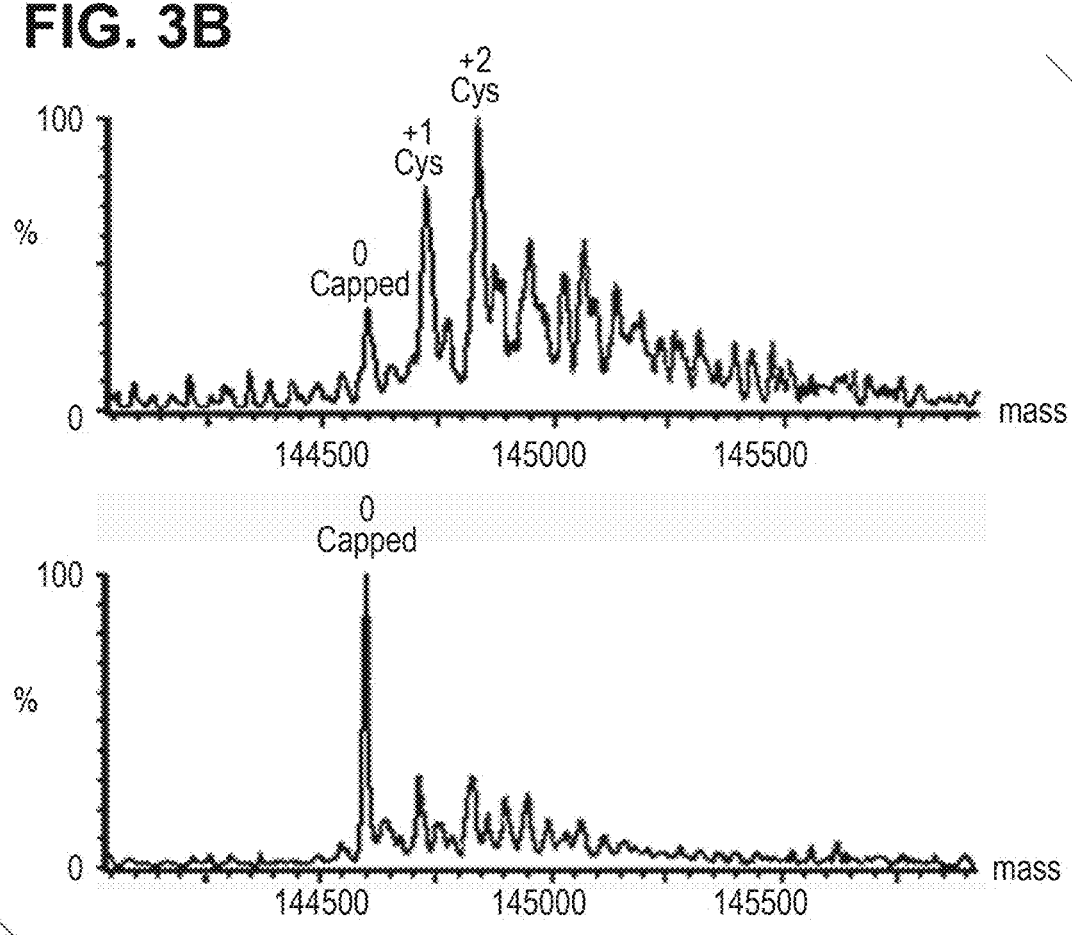
FIG. 3B: Mass spec analysis of cysteine mutant antibody as shown in FIG. 3A.

Example 5: Generation of Fully Uncapped Cysteine Mutant Antibody Via HEK293 Transient Expression in Zero or Low Cysteine-, Cystine- and Glutathione-Media The finding that adding excess cysteine or glutathione in culture media affects the capping status of cysteine mutant antibodies suggests cysteine capping takes place outside of the cell. To investigate this further a medium lacking cysteine, cystine and glutathione (a so-called "triple-low" medium) was generated. Without being limited to a particular theory, it was suspected that If cysteinylation and glutathionylation occurred within the cell (as was commonly speculated) substantial cysteinylated or glutathionylated antibody should still be detected in antibodies generated using triple-low medium, since ER lumen have sufficient cysteine, cystine and glutathione (synthesizable from other medium components, such as serine and methionine). Conversely, if cysteinylation and glutathionylation occurred outside the cell the cysteine mutant antibody should be fully uncapped when produced in the triple-low medium, as there is no capping source available in the medium. HEK293 cells in regular FreeStyle™ 293 expression medium were transfected and then re-suspended into either fresh FreeStyle™ 293 expression medium (control) or triple-low medium. Transfection was completed at 24 hr. At 96 h cell viability was measured and conditioned medium was harvested. For the triple-low medium, culture cell viability 50%, while cell viability was 80% in the FreeStyle™ 293 expression medium. (This viability observation is not unexpected. Even though Cys is a nonessential amino acid, cells would still need time to adapt to the changes of lacking direct supply of Cys). Protein expression in the triple-low medium was 5-fold lower than those in the regular medium, as protein synthesis was likely slowed due to the lack of the immediate cysteine supply. Antibody purification from ProA column and protein migration in SDS-PAGE were nearly identical (data not shown). FIG. 3A shows the SEC data, which indicates nearly identical chromatography with less than 1% protein aggregation. Then the protein samples were analyzed in Mass Spec for their capping status measurement. As shown in FIG. 3B, while regular medium gave a similar heterogeneous capping mixture, interestingly, the triple-low medium produced only fully uncapped species—cysteinylated species were not present. This data indicates that in HEK293 cells, cysteinylation capping appears to occur outside the cells.

Figure 4A:
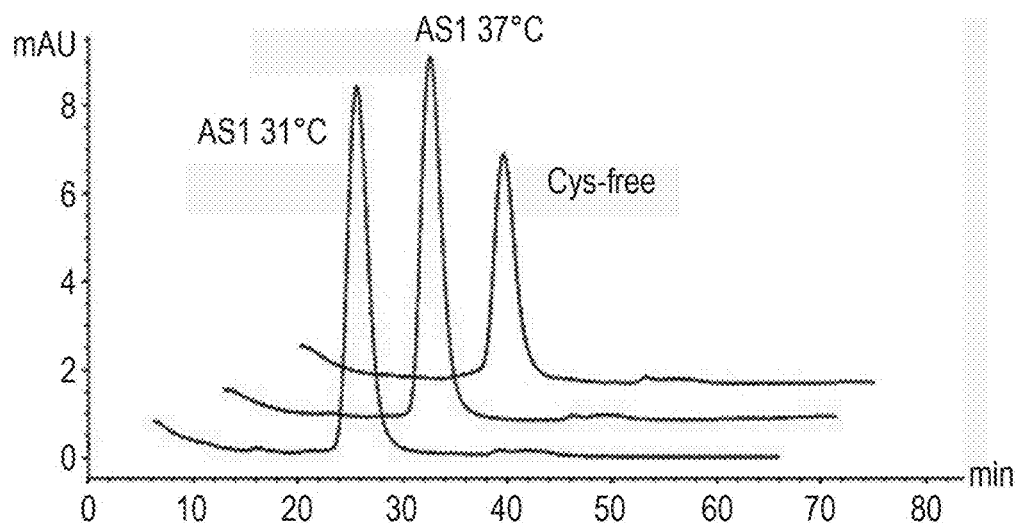
FIG. 4A: SEC analysis of cysteine mutant antibody expressed in stable CHO-DUKX in triple-low medium.
Figure 4B:
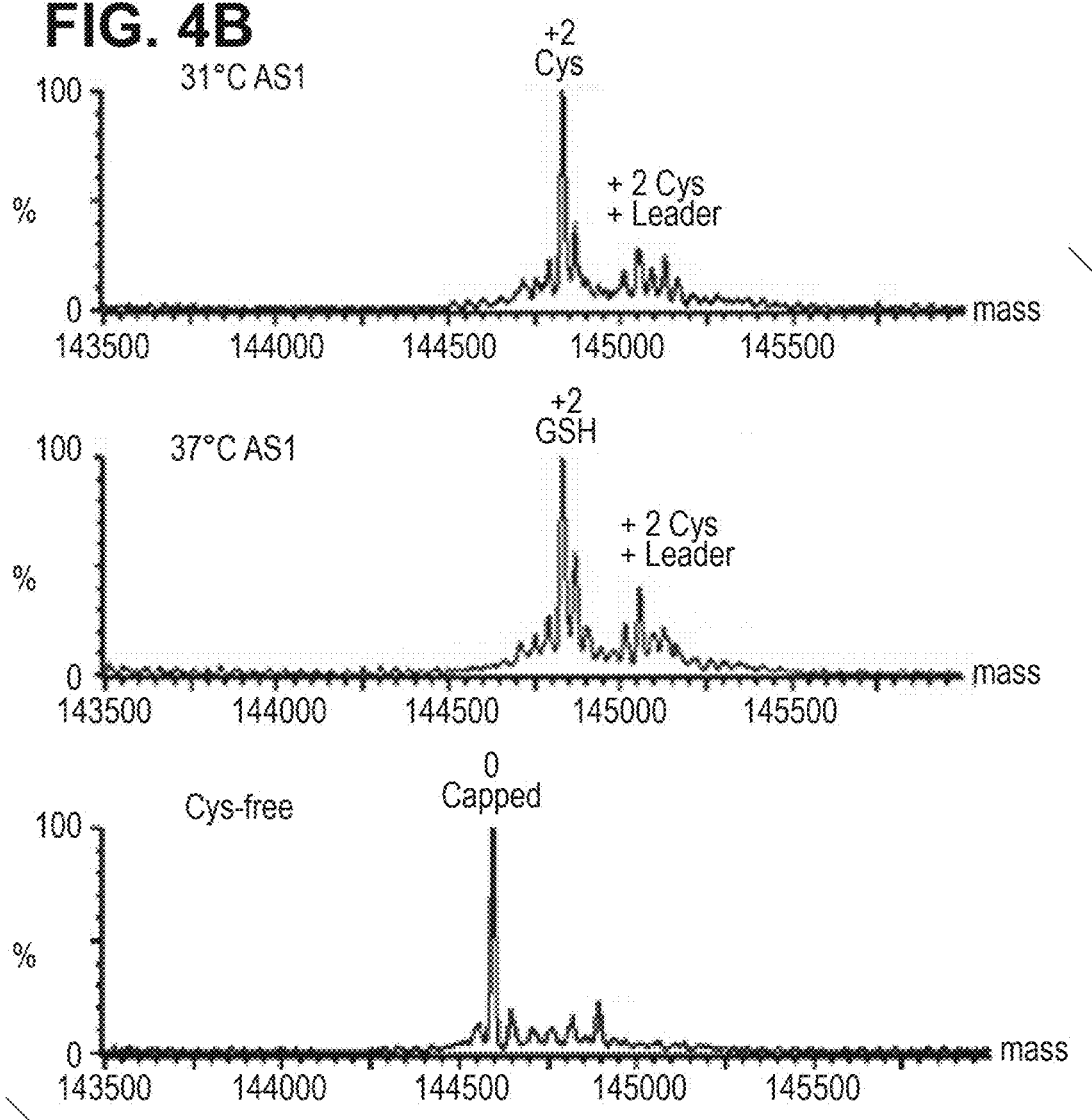
FIG. 4B: Mass spec analysis of cysteine mutant antibody as shown in FIG. 4A.

Example 6: Generation of Fully Uncapped Cysteine Mutant Antibodies Via Stable CHO Expression in Zero or Low Cysteine-, Cystine- and Glutathione Medium To rule out the possibility that the observations of Example 5 were cell-line specific or related to transient expression, the experiment was repeated using the stable CHO-DUKX line. The CHO-DUKX cell line, which stably expresses the cysteine mutant antibody was grown in CD-CHO medium to 4×10e6/ml, then these cells were switched to either CD-CHO medium (control) or the triple-low medium. One more control is the fresh CD-CHO medium culturing at 31° C. instead of 37° C. At 72 hrs, cell viability was measured and conditioned medium was harvested. For cells grown in triple-low medium cell viability of stable CHO cells was 60%. Cell viability for cells grown in the CD-CHO medium was more than 95%. Protein expression in the triple-low medium was nearly 5-fold lower than those in the CD-CHO medium, likely due to the lack of cysteine in the medium. Antibody purification from ProA column and protein migration in SDS-PAGE from both media were nearly identical (data not shown). FIG. 4A shows a similar SEC data with very little aggregation. The protein samples were analyzed by mass spec to measure capping. As shown in FIG. 4B, for CD-CHO medium, the cysteine mutant antibody was fully cysteinylated either at 37° C. or 31° C., indicating that culturing temperatures did not affect capping status. In triple-low medium stable CHO cells produced fully uncapped cysteine mutant protein. Thus in CHO cells cysteinylation capping appears to occur outside the cells. This data confirms that generation of fully uncapped cysteine mutant antibody in triple-low medium is not cell-type specific.

Example 7: Direct Conjugation of Uncapped Cysteine Mutant Antibodies

Figure 13:
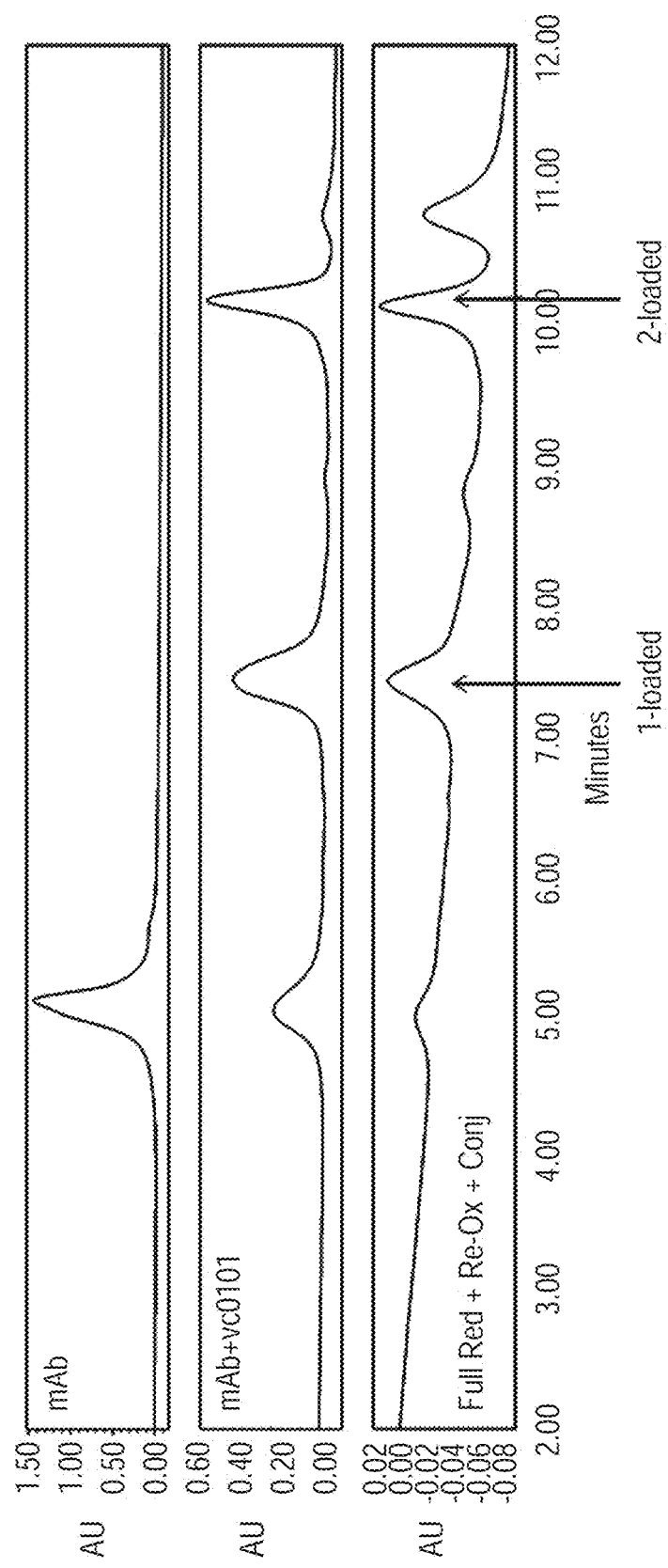
FIG. 13. HIC Profile Showing Direct Conjugation of Uncapped Antibody with mcvcPABC0101. For comparison the HIC profiles of the antibody and ADC synthesized by conventional protocol (total reduction followed by re-oxidation and conjugation) are shown.

To 0.5 mg (3.45 nmol; 10.19 mg/mL; 49.07 µL) IL13Ra2 L443C uncapped mAb from Example 6 in 20 mM histidine, pH 5.8 buffer was added 32.0 µg of mcvcPABC0101 linker-payload (10 equivalents, 34.52 nmol; 10 mM in dimethylsulfoxide; 1.7 μL). The reaction mixture was incubated at 25° C., 1 h. A hydrophobic interaction chromatography (HIC) assay was used to analyze reaction mixture. See FIG. 13, which compares HIC chromatograms for the Example 7 ADC with the corresponding unconjugated antibody, and the the corresponding ADC prepared by conventional methods.

Example 8: Nitrothiobenzoate-Capped Cys-Mutant K290C Antibody is Efficiently Generated with HEK293F Transient Expression System in Cysteine-Containing Normal Medium FreeStyle™ when DTNB Addition to Cell Culture is Titrated To determine if nitrothiobenzoate-capping can be generated under normal cell culture medium during HEK293F transient expression, various concentrations of DTNB solutions were added to HEK293F culture post DNA transfection. Briefly, HEK293F cells were grown to around 1.0e6/ml in FreeStyle™ medium, 1 mg of DNAs (0.5 mg heavy chain DNA and 0.5 mg light chain DNA of a Cys-mutant K290C antibody) was mixed with 3.5 mg of transfection agent for 20 min-incubation at room temperature. The mixture was inoculated with 1 L of HEK293F cells and the transfected cells were cultured at 37° C. At 16 hrs post-transfection, a final concentration of DTNB at 0.5 mM, or 1 mM, or 2 mM, or 3 mM, or 4 mM, or 6 mM was inoculated from a stock concentration of 40 mM into 50 ml-cell culture aliquots of the 1 L transfected cell culture. Such cell culturing continued for additional 5 days. Conditioned media were harvested and filtered, and subjected to a 1 ml-ProA column purification. Protein elutions were dialyzed against PBS buffer, and concentrated through centricon.

Figure 16:
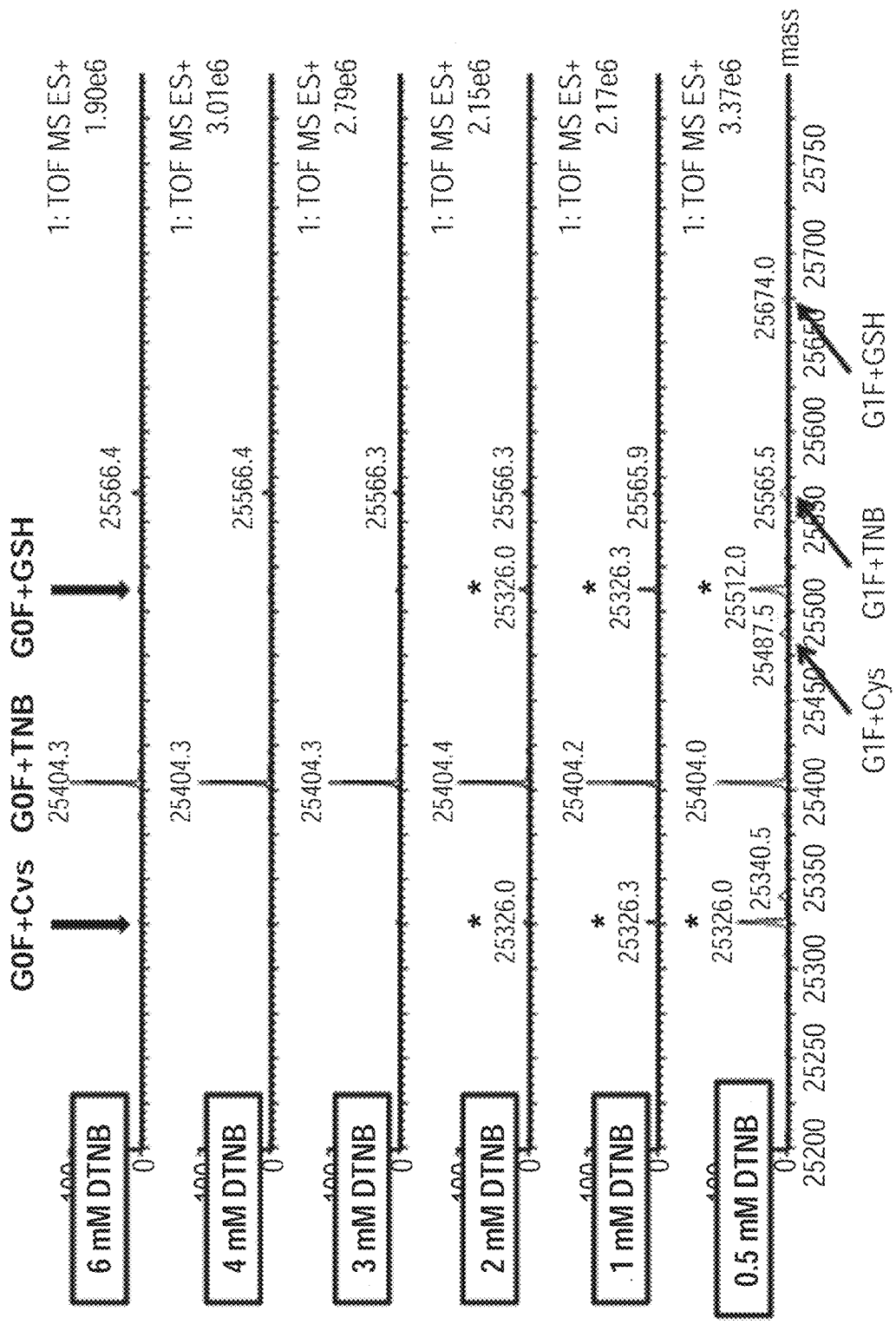
FIG. 16. Nitrothiobenzoate-capped Cys-mutant K290C antibody is efficiently generated with HEK293F transient expression system in normal cysteine-containing medium when DTNB addition to cell culture is titrated. Mass spec analysis of cysteine mutant antibody digested with Ides enzyme for Fc portion of K290C cysteine mutant antibody.
Figure 17:
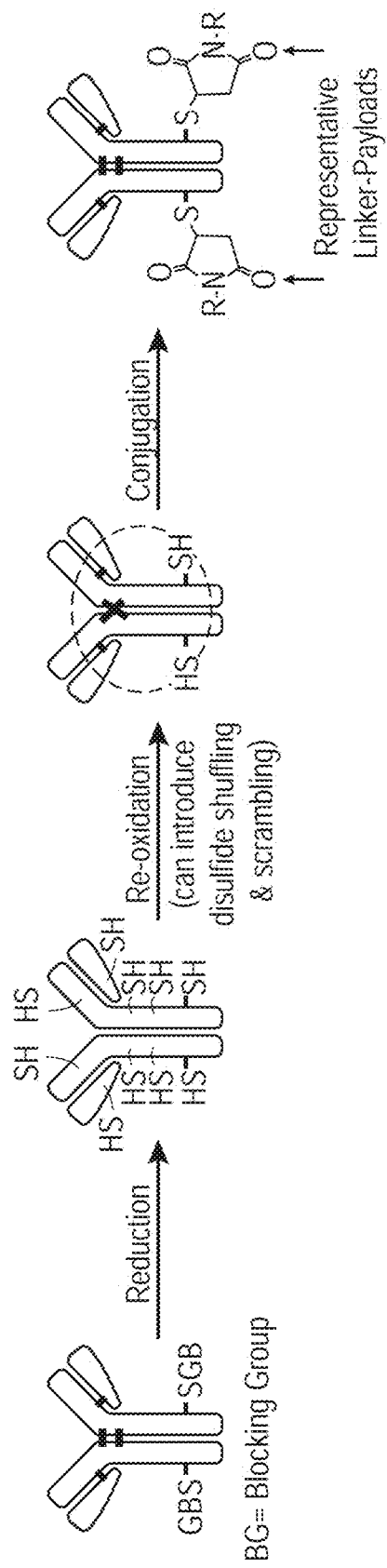
FIG. 17. Depiction of di-sulfide shuffling within an antibody due to reduction and re-oxidation.
Figure 18:
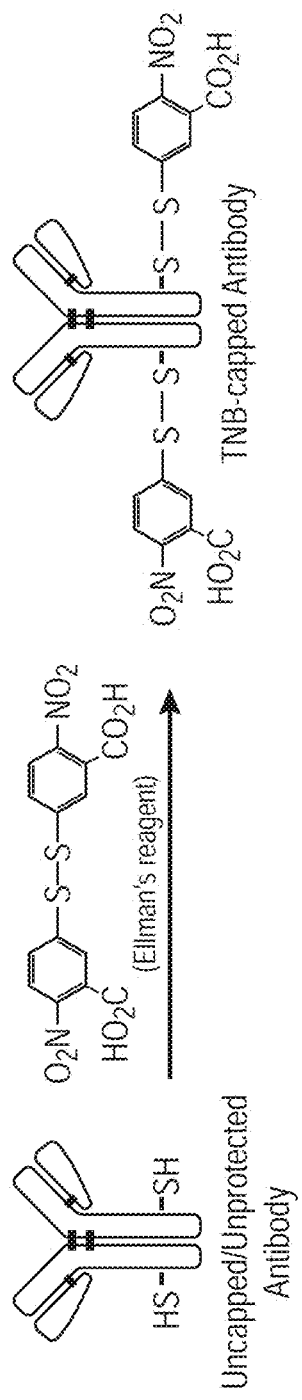
FIG. 18. Depiction of antibody capping with TNB.
Figure 19:
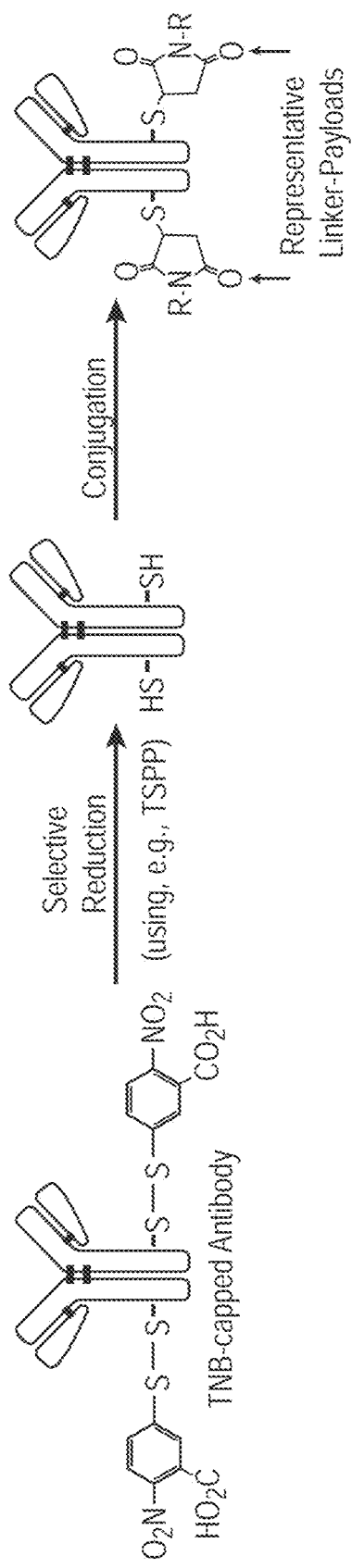
FIG. 19. Depiction of the removal of TNB capping and simultaneous conjugation with TSPP.
Figure 21:
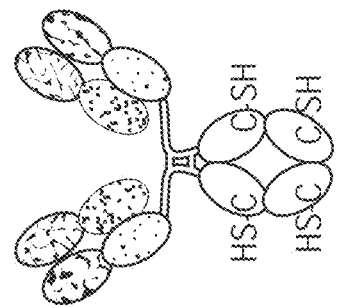
FIG. 21. Diagram of uncapped cysteine residues in an antibody.
Figure 20:
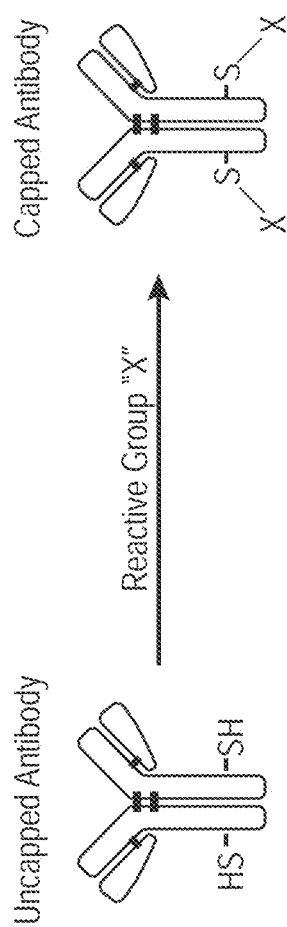
FIG. 20. Depiction of engineered capping agents useful as "chemical handles" for drug conjugation chemistry.

As shown in FIG. 16, the mass spec data indicates that with an increase of DTNB concentration, the protein species with thionitrobenzoate capping (mass increase of ~396 Da) was drastically improved. At the concentration of higher than 3 mM DTNB, nearly all protein species were thionitrobenzoate-capped. This result indicates that thionitrobenzoate-capping can be generated during HEK293F transient expression in normal culture medium with cysteine, and that thionitrobenzoate-capping generation seems to be much more efficient than that of cysteinylation capping.

We claim:

1. A method of producing an antibody drug conjugate (ADC) comprising the steps:
   (a) producing a capped antibody in a cell culture, wherein one or more unpaired cysteine residues on said antibody are covalently bonded through sulfur bonds to one or more predetermined capping moieties, wherein said predetermined capping moieties are selected from the group consisting of 5-thio-2-nitrobenzoic acid (TNB), 2-mercaptopyridine and dithiodipyridine (DTDP);
   (b) exposing said capped antibody to a reducing agent capable of removing said capping moieties from said antibody without reducing antibody inter-chain sulfur bonds, wherein said reducing agent is tris (3-sulfophenyl) phosphine (TSPP):

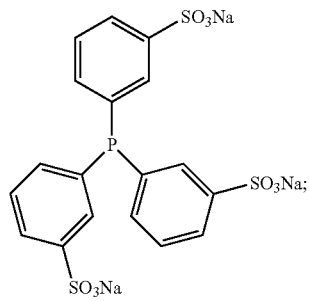

and
   (c) without introducing an oxidizing agent, conjugating one or more reduced sulfur bonds on said antibody to a payload via a linking moiety, wherein said payload is an auristatin, a spliceostatin or a calicheamicin.

2. The method of claim 1 wherein said predetermined capping moieties are 5-thio-2-nitrobenzoic acid (TNB).

3. The method of claim 1 wherein said reduction occurs primarily at unpaired cysteine residues.

4. The method of claim 1, wherein said auristatin is selected from (2-Methylalanyl-N-[(3R,4S,5S)-3-methoxy-1-{(2S)-2-[(1R,2R)-1-methoxy-2-methyl-3-oxo-3-{[(1 S)-2-phenyl-1-(1,3-thiazol-2-yl)ethyl]amino}propyl]pyrrolidin-1-yl}-5-methyl-1-oxoheptan-4-yl]-N-methyl-L-valinamide); (2-Methylalanyl-N-[(3R,4S,5S)-1-{(2S)-2-[(1R, 2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide); (2-methyl-L-prolyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3 oxopropyl]pyrrolidin-1-yl}-5-methyl-1-oxoheptan-4-yl]-N-methyl-L-valinamide, trifluoroacetic acid salt); (2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide); (2-methylalanyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide); (2-methyl-L-prolyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt); monomethyl dolastatin 10; (N-methylvaline-valine-dolaisoleuine-dolaproine-norephedrine); and (N-methylvaline-valine-dolaisoleuine-dolaproine-phenylalanine).

5. The method of claim 1, wherein said cell culture contains a precursor of a capping moiety and wherein said precursor of said capping moiety is Ellman's reagent.

6. A method of producing an antibody drug conjugate (ADC) comprising the steps:
   (a) producing a capped antibody in a cell culture, wherein one or more unpaired cysteine residues on said antibody are covalently bonded through sulfur bonds to one or more predetermined capping moieties, wherein said predetermined capping moieties are selected from the group consisting of 5-thio-2-nitrobenzoic acid (TNB), 2-mercaptopyridine and dithiodipyridine (DTDP);
   (b) exposing said capped antibody to a reducing agent capable of removing said capping moieties from said antibody without reducing antibody inter-chain sulfur bonds, wherein said reducing agent is tris (3-sulfophenyl) phosphine (TSPP):

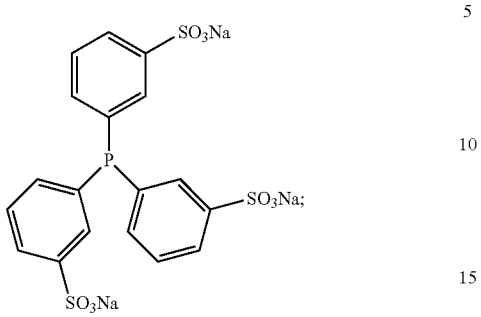

and
(c) without introducing an oxidizing agent, conjugating one or more reduced sulfur bonds on said antibody to a payload via a linking moiety, wherein said payload is the auristatin (2;-Methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl[N-methyl-L-valinamide).

* * * * *